(12) United States Patent
Moser et al.

(10) Patent No.: US 11,529,246 B2
(45) Date of Patent: Dec. 20, 2022

(54) PROSTHETIC ANKLE AND FOOT COMBINATION

(71) Applicant: Blatchford Products Limited, Hampshire (GB)

(72) Inventors: David Moser, Hampshire (GB); Andrew John Sykes, Surrey (GB); Graham Harris, Hampshire (GB); Stephen Terry Lang, Hampshire (GB); Fadi Abimosleh, Springboro, OH (US); Mir Saeed Zahedi, London (GB)

(73) Assignee: Blatchford Products Limited, Hampshire (GB)

( * ) Notice: Subject to any disclaimer, the term of this patent is extended or adjusted under 35 U.S.C. 154(b) by 346 days.

(21) Appl. No.: 16/185,808

(22) Filed: Nov. 9, 2018

(65) Prior Publication Data

US 2019/0142611 A1 May 16, 2019

Related U.S. Application Data

(63) Continuation of application No. 14/823,645, filed on Aug. 11, 2015, now Pat. No. 10,130,495, which is a
(Continued)

(51) Int. Cl.
*A61F 2/70* (2006.01)
*A61F 2/66* (2006.01)
(Continued)

(52) U.S. Cl.
CPC .............. *A61F 2/6607* (2013.01); *A61F 2/70* (2013.01); *A61F 2/74* (2021.08); *A61F 2/748* (2021.08);
(Continued)

(58) Field of Classification Search
CPC .. A61F 2/60; A61F 2/66; A61F 2/6607; A61F 2/68; A61F 2/70; A61F 2/74; A61F 2002/5006
See application file for complete search history.

(56) References Cited

U.S. PATENT DOCUMENTS

| 37,637 A | 2/1863 | Parmelee |
| 2,470,480 A | 5/1949 | Fogg |

(Continued)

FOREIGN PATENT DOCUMENTS

| CN | 101518473 A | 9/2009 |
| DE | 818 828 | 10/1951 |

(Continued)

OTHER PUBLICATIONS

"Anatomic and Biomechanical Characteristics of the Ankle Joint and Total Ankle Arthroplasty", Total Ankle Arthroplasty, Dec. 5, 2005, Springer Vienna, ISBN 978-3-211-21252 (print) 978-3-211-27254-1 (online), pp. 25-42.
(Continued)

*Primary Examiner* — Bruce E Snow
(74) *Attorney, Agent, or Firm* — Alston & Bird LLP

(57) ABSTRACT

A prosthetic ankle and foot combination has an ankle joint mechanism constructed to allow damped rotational movement of a foot component relative to a shin component. The mechanism provides a continuous hydraulically damped range of ankle motion during walking with dynamically variable damping resistances, and with independent variation of damping resistances in the plantar-flexion and dorsi-flexion directions. An electronic control system coupled to the ankle joint mechanism includes at least one sensor for generating signals indicative of a kinetic or kinematic parameter of locomotion, the mechanism and the control system being arranged such that the damping resistances effective over the range of motion of the ankle are adapted
(Continued)

automatically in response to such signals. Single and dual piston hydraulic damping arrangements are disclosed, including arrangements allowing independent heel-height adjustment.

10 Claims, 13 Drawing Sheets

Related U.S. Application Data continuation of application No. 13/150,694, filed on Jun. 1, 2011, now Pat. No. 9,132,023, which is a continuation of application No. 12/035,717, filed on Feb. 22, 2008, now Pat. No. 7,985,265, which is a continuation-in-part of application No. 11/956,391, filed on Dec. 14, 2007, now Pat. No. 8,574,312.

(60) Provisional application No. 60/891,075, filed on Feb. 22, 2007, provisional application No. 60/869,959, filed on Dec. 14, 2006.

(51) Int. Cl.
- *A61F 2/50* (2006.01)
- *A61F 2/30* (2006.01)
- *A61F 2/68* (2006.01)
- *A61F 2/76* (2006.01)
- *A61F 2/74* (2006.01)

(52) U.S. Cl.
CPC ............... *A61F 2002/30359* (2013.01); *A61F 2002/5006* (2013.01); *A61F 2002/5018* (2013.01); *A61F 2002/5033* (2013.01); *A61F 2002/5035* (2013.01); *A61F 2002/5036* (2013.01); *A61F 2002/5038* (2013.01); *A61F 2002/5043* (2013.01); *A61F 2002/6614* (2013.01); *A61F 2002/6621* (2013.01); *A61F 2002/6642* (2013.01); *A61F 2002/6657* (2013.01); *A61F 2002/6854* (2013.01); *A61F 2002/704* (2013.01); *A61F 2002/708* (2013.01); *A61F 2002/764* (2013.01); *A61F 2002/7625* (2013.01); *A61F 2220/0033* (2013.01)

(56) References Cited

U.S. PATENT DOCUMENTS

| | | | |
|---|---|---|---|
| 2,490,796 A | 12/1949 | Gettman et al. |
| 2,541,234 A | 2/1951 | Fulton |
| 2,657,393 A | 11/1953 | Haller |
| 2,699,554 A | 1/1955 | Comelli |
| 2,843,853 A | 7/1958 | Mauch |
| 2,851,694 A | 9/1958 | Valenti |
| 3,659,294 A | 5/1972 | Glabiszewski |
| 3,871,032 A | 3/1975 | Karas |
| 4,010,829 A | 3/1977 | Naito et al. |
| 4,051,558 A | 10/1977 | Vallotton |
| 4,212,087 A | 7/1980 | Mortensen |
| 5,030,239 A | 7/1991 | Copes |
| 5,044,360 A | 9/1991 | Janke |
| 5,116,383 A | 5/1992 | Shorter et al. |
| 5,383,939 A | 1/1995 | James |
| 5,458,656 A | 10/1995 | Phillips |
| 5,913,901 A | 6/1999 | Lacroix |
| 5,957,981 A | 9/1999 | Gramnas |
| 6,033,440 A | 3/2000 | Schall et al. |
| 6,080,197 A | 6/2000 | Chen |
| 6,113,642 A | 9/2000 | Petrofsky et al. |
| 6,187,052 B1 | 2/2001 | Molino et al. |
| 6,398,817 B1 | 6/2002 | Hellberg et al. |
| 6,443,993 B1 | 9/2002 | Koniuk |
| 6,517,585 B1 | 2/2003 | Zahedi et al. |
| 6,863,695 B2 | 3/2005 | Doddroe et al. |
| 7,341,603 B2 | 3/2008 | Christensen |
| 7,507,259 B2 | 3/2009 | Townsend et al. |
| 7,611,542 B2 | 11/2009 | Bourne et al. |
| 7,883,548 B2 | 2/2011 | Lang et al. |
| 7,985,265 B2 | 7/2011 | Moser et al. |
| 8,246,695 B2 | 8/2012 | Mosler |
| 2002/0052663 A1 | 5/2002 | Herr et al. |
| 2002/0082712 A1 | 6/2002 | Townsend et al. |
| 2002/0120349 A1 | 8/2002 | Phillips |
| 2002/0138153 A1* | 9/2002 | Koniuk ............. A61F 2/68 623/24 |
| 2004/0044417 A1 | 3/2004 | Gramnas |
| 2004/0054423 A1 | 3/2004 | Martin |
| 2004/0064195 A1 | 4/2004 | Herr |
| 2004/0236435 A1 | 11/2004 | Chen |
| 2005/0015157 A1 | 1/2005 | Doddroe et al. |
| 2005/0109563 A1 | 5/2005 | Vitale et al. |
| 2005/0192677 A1 | 9/2005 | Ragnarsdottir et al. |
| 2005/0267601 A1 | 12/2005 | Chen |
| 2006/0069448 A1 | 3/2006 | Yasui |
| 2006/0069449 A1 | 3/2006 | Bisbee, III et al. |
| 2006/0235544 A1 | 10/2006 | Iversen et al. |
| 2006/0249315 A1 | 11/2006 | Herr et al. |
| 2007/0043449 A1 | 2/2007 | Herr et al. |
| 2007/0073514 A1 | 3/2007 | Nogimori et al. |
| 2008/0004718 A1 | 1/2008 | Mosler |
| 2008/0262635 A1 | 10/2008 | Moser et al. |
| 2008/0281435 A1 | 11/2008 | Abimosleh et al. |
| 2008/0300692 A1 | 12/2008 | Moser et al. |
| 2008/0306612 A1 | 12/2008 | Mosler |
| 2009/0030530 A1 | 1/2009 | Martin |
| 2012/0130508 A1 | 5/2012 | Harris et al. |
| 2014/0039645 A1 | 2/2014 | Moser et al. |
| 2014/0067086 A1 | 3/2014 | Moser et al. |
| 2014/0379096 A1 | 12/2014 | Zahedi et al. |
| 2021/0205100 A1* | 7/2021 | Pusch ................. A61F 2/68 |

FOREIGN PATENT DOCUMENTS

| | | |
|---|---|---|
| DE | 21 01 303 A1 | 6/1972 |
| EP | 0 549 855 B1 | 3/1996 |
| EP | 0 948 947 A2 | 10/1999 |
| EP | 1 068 844 A1 | 1/2001 |
| GB | 643734 | 9/1950 |
| GB | 2 234 907 A | 2/1991 |
| GB | 2 305 363 | 4/1997 |
| GB | 2 328 160 A | 2/1999 |
| JP | 59183747 | 10/1984 |
| JP | 59189843 | 10/1984 |
| JP | 2001-514925 A | 9/2001 |
| JP | 2004-506480 A | 3/2004 |
| JP | 2008-536614 A | 9/2008 |
| JP | 2009-515628 A | 4/2009 |
| WO | WO 93/06795 A1 | 4/1993 |
| WO | WO 96/25898 A1 | 8/1996 |
| WO | WO 99/00075 A1 | 1/1999 |
| WO | WO 00/76429 A1 | 12/2000 |
| WO | WO 02/15826 A1 | 2/2002 |
| WO | WO 03/086245 A2 | 10/2003 |
| WO | WO 2006/112774 A1 | 10/2006 |
| WO | WO 2007/027808 A2 | 3/2007 |
| WO | WO 2007/054736 A2 | 5/2007 |
| WO | WO 2008/071975 A1 | 6/2008 |
| WO | WO 2008/103917 A1 | 8/2008 |
| WO | WO 2012/104591 A1 | 8/2012 |

OTHER PUBLICATIONS

Combined Search and Examination Report for Great Britain Application No. GB 1201875.0 dated Apr. 12, 2012.
Decision, IPR2015-00640, U.S. Pat. No. 8,740,991 B2, dated Jul. 31, 2015, 29 pages.
Decision, IPR20 15-00641, U.S. Pat. No. 8,574,312 B2, dated Jul. 31, 2015, 29 pages.
Decision, IPR2015-00642, U.S. Pat. No. 8,574,312 B2, dated Jul. 31, 2015, 25 pages.

(56) References Cited

OTHER PUBLICATIONS

Endolite Global—Echelon VT Foot—Prescription [online][retrieved May 7, 2012]. Retrieved from the Internet: <URL: http://www.endolite.co.uk/products/feet/echelon_vt/echelon_vt_foot.html> 1 page.
Extended European Search Report for European Application No. 18 17 4391 dated Nov. 29, 2018, 6 pages.
Furman, Bess; "Progress in Prosthetics", U.S. Department of Health, Education, and Welfare; 1964.
Hayes, W. C. et al., *Leg Motion Analysis During Gait by Multitaxial Accelerometry: Theoretical Foundations and Preliminary Validations*, Journal of Biomechanical Engineering, vol. 105 (1983) 283-289.
Hydraulik Ankle Unit Manual; Mauch Laboratories, Inc., Mar. 1988.
International Search Report and Written Opinion for International Application No. PCT/GB2007/004785, dated Apr. 29, 2008.
International Search Report and Written Opinion for International Application No. PCT/GB2012/000112, dated Apr. 24, 2012.
International Search Report and Written Opinion for International Application No. PCT/US2008/054741, dated Jul. 2, 2008.
Michael, J. et al.; "Hip Disarticulation and Transpelvic Amputation: Prosthetic Management"; Atlas of Limb Prosthetics: Surgical, Prosthetic, and Rehabilitation Principles, 2nd edition, Ch. 21B; 1992.
Morris, J. W.; "Accelerometry—A Technique for the Measurement of Human Body Movements" Journal of Biomechanics (1973) 726-736.
Murphy, Eugene F.; "The Swing of Walking with Above-Knee Prostheses" Bulletin of Prosthetics Research, Veterans Administration; Spring 1964.
Notice of Allowance for U.S. Appl. No. 14/823,645 dated July 6, 2018.
Notice of Allowance for U.S. 15/227,514 dated Feb. 21, 2018.
Office Action for European Application No. 07 848 527.3 dated Feb. 25, 2014, 6 pages.
Office Action for European Application No. 08 730 531.4 dated Feb. 27, 2017.
Office Action for European Application No. 08 730 531.4 dated Jun. 17, 2016, 3 pages.
Office Action for European Application No. 08 730 531.4 dated Mar. 21, 2014, 4 pages.
Office Action for Japanese Application No. 2009-551033 dated Sep. 11, 2012.
Office Action for U.S. Appl. No. 15/227,514 dated Nov. 9, 2017.
Office Action for U.S. Appl. No. 11/956,391; dated July 30, 2013.
Office Action for U.S. Appl. No. 11/956,391; dated Jul. 5, 2012.
Office Action for U.S. Appl. No. 11/956,391; dated Jun. 18, 2010.
Office Action for U.S. Appl. No. 11/956,391; dated May 10, 2011.
Office Action for U.S. Appl. No. 11/956,391; dated Sep. 16, 2013.
Office Action for U.S. Appl. No. 11/956,391; dated Sep. 18, 2009.
Office Action for U.S. Appl. No. 12/035,717; dated Apr. 21, 2010.
Office Action for U.S. Appl. No. 12/035,717; dated Aug. 5, 2009.
Office Action for U.S. Appl. No. 13/150,694, dated Dec. 17, 2014.
Office Action for U.S. Appl. No. 13/150,694, dated Dec. 30, 2013.
Office Action for U.S. Appl. No. 13/150,694, dated Dec. 4, 2012.
Office Action for U.S. Appl. No. 13/150,694, dated Jul. 19, 2013.
Office Action for U.S. Appl. No. 13/150,694, dated May 9, 2014.
Office Action for U.S. Appl. No. 13/364,786, dated May 22, 2013.
Office Action for U.S. Appl. No. 14/051,775 dated Jun. 12, 2015.
Office Action for U.S. Appl. No. 14/051,775 dated Nov. 25, 2014.
Office Action for U.S. Appl. No. 14/073,394; dated Jan. 28, 2014.
Office Action for U.S. Appl. No. 14/823,645 dated Feb. 1, 2018.
Office Action for U.S. Appl. No. 14/823,645, dated May 30, 2017, 30 pages.
Office Action for U.S. Appl. No. 15/227,514 dated Apr. 26, 2017, 21 pages.
Roylance, David; "Engineering Viscoelasticity" Department of Materials Science and Engineering, Massachusetts Institute of Technology; Oct. 24, 2001.
Search Report for Great Britain Application No. 1101893.4 dated May 11, 2011.
Segal, et al.; "Kinematic Comparisons of Transfemoral Amputee Gait Using C-Leg and Mauch SNS Prosthetic Knees;" The Journal of Rehabilitation Research and Development, vol. 43, No. 7; pp. 857-870; dated Nov./Dec. 2006; Figure 3.
Sowell, T.T.; "A preliminary clinical evaluation of the Mauch hydraulic foot-ankle system"; Prosthetics and Orthotics International; vol. 5, pp. 87-91; 1987.
Starker, Felix et al.; "Remaking the Mauch Hydraulic Ankle", Capabilities, vol. 18 No. 1, Winter 2010; Northwestern University.
Wagner, Edmnond M.; "Contributions of the Lower-Extremity Prosthetics Program", Artificial Limbs: A Review of Current Developments; National Academy of Sciences National Research Council; May 1954.
Winter, David A.; Kinematics 1.3.2 and Kinetics 1.3.3; Biomechanics and Motor Control of Human Movement, Fourth Edition; 2009; 3 pages.
Office Action for U.S. Appl. No. 16/010,829 dated Oct. 29, 2019, 17 pages.
Extended European Search Report for EP No. 20157507.7 dated Sep. 14, 2020 (6 pages).

* cited by examiner

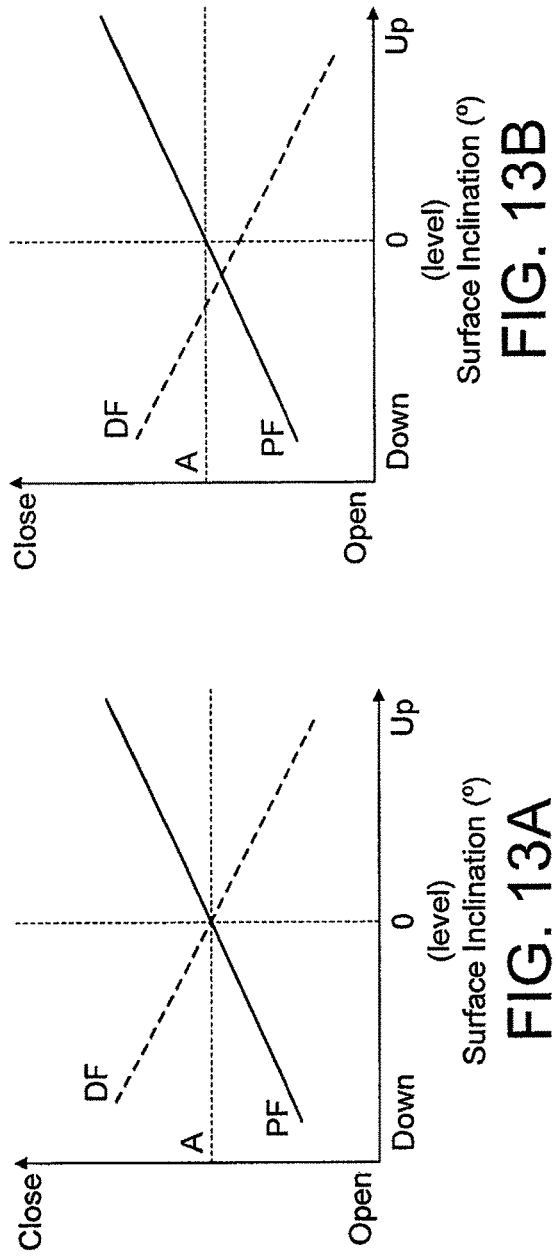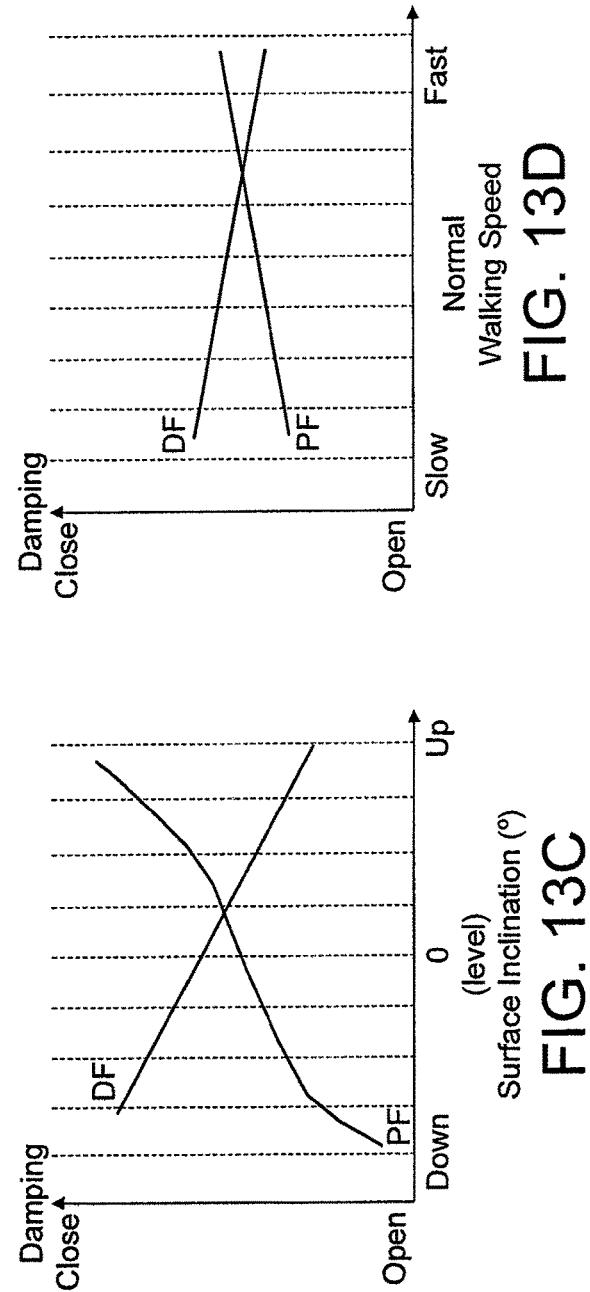
FIG. 13A
FIG. 13B
FIG. 13C
FIG. 13D

PROSTHETIC ANKLE AND FOOT COMBINATION

CROSS-REFERENCE TO RELATED APPLICATIONS

This is a continuation of U.S. application Ser. No. 14/823, 645 (issued as U.S. Pat. No. 10,130,495 on Nov. 20, 2018), filed Aug. 11, 2015, which is a continuation of U.S. application Ser. No. 13/150,694 (issued as U.S. Pat. No. 9,132, 023 on Sep. 15, 2015), filed Jun. 1, 2011, which is a continuation of U.S. application Ser. No. 12/035,717 (issued as U.S. Pat. No. 7,985,265 on Jul. 26, 2011), filed Feb. 22, 2008, which claims the benefit of Provisional Application No. 60/891,075, filed Feb. 22, 2007. U.S. application Ser. No. 12/035,717 is a continuation-in-part of U.S. application Ser. No. 11/956,391 (issued as U.S. Pat. No. 8,574,312 on Nov. 5, 2013), filed Dec. 14, 2007, which claims the benefit of Provisional Application No. 60/869,959, filed Dec. 14, 2006. The entire contents of each of the foregoing applications are incorporated by reference in the present application.

FIELD OF THE INVENTION

This invention relates to a prosthetic ankle and foot combination arranged to allow damped ankle flexion. The invention also includes a lower limb prosthesis incorporating such an ankle and foot combination.

BACKGROUND OF THE INVENTION

Current prosthetic ankle-foot systems are generally aligned for operation as fixed mechanical structures comprising elastic and deformable elements designed to provide stability during standing and walking and to return energy for propulsion into the swing phase of the walking cycle. However, such a device is often uncomfortable for the user whilst standing and walking on ramps and stairs and walking at different speeds. Users have also experienced knee instability and difficulty in maintaining forward motion during roll-over of the foot while standing and walking on ramps and stairs, with consequent impairment of efficiency. These difficulties are particularly important for transfemoral amputees whose stance phase action is normally compromised by significantly reduced knee flexion and extension which would otherwise assist shock absorption and forwards propulsion during the stance phase.

Another aspect of ankle-foot function and transfemoral amputee locomotion relates to the way in which a typical known prosthesis hinders the amputee, resulting in poor body posture for certain locomotion activities such as ascending and descending stairs and ramps, which diminishes the potential for application of voluntary control, particularly user-generated hip extension torque. The poor posture described is largely caused by inappropriate stiffness and range of motion at the ankle which does not allow the body centre of mass to pass easily over the ankle. Consequently, amputees sometimes have to adopt unnatural compensating actions.

An ankle joint mechanism allowing dynamic hydraulic control of the angular position of a prosthetic foot with respect to a shin component is disclosed in Mauch Laboratories, Inc., Hydraulik Ankle Unit Manual, March 1988. The shin component is attached to a vane piston housed in a fluid-filled chamber with a concave part-circular lower wall. A gravity-controlled ball rolls forwards and backwards on the wall according to the orientation of the foot to open or close a bypass passage in the piston. As a result, dorsi-flexion of the mechanism is prevented when the shin component is vertical, largely irrespective of whether the foot is horizontal or inclined downwardly or upwardly. Such a prosthesis also suffers partly from the disadvantages described above.

In US2002/0138153 (Koniuk) a self-adjusting ankle with a similar function is disclosed. This unit switches between two damping resistance levels, the switch between the two damping levels being triggered by detection of a shin pylon reaching a vertical orientation. The second damping level is set effectively to prevent pivoting of the foot.

Amongst other known prosthetic ankle systems is that of U.S. Pat. No. 3,871,032 (Karas). This system contains a damping device having a dual piston and cylinder assembly with tappet return springs acting continuously to return the ankle to a neutral position. EP-A-0948947 (O'Byrne) discloses a prosthetic ankle having a ball-and-socket joint with a chamber filled with a silicone-based hydraulic substance, the joint having a visco-elastic response. In one embodiment, the chamber contains solid silicone rubber particles suspended in a silicone fluid matrix. US2004/0236435 (Chen) discloses a hydraulic ankle arrangement with adjustable hydraulic damping and resilient biasing members mounted anteriorly and posteriorly of an ankle joint rotation axis. In WO00/76429 (Gramtec), a leg prosthesis is described having an ankle joint allowing heel height adjustment by way of a hydraulic piston and linkage arrangement. Elastic components absorb shock during walking. US2006/0235544 (Iversen et al) discloses a hydraulic ankle mechanism with a rotary vane.

The electronically controlled ankle disclosed in WO2003/086245 (Martin) has a magnetorheological (MR) fluid-controlled ankle component. WO2007/027808 (Ossur) discloses an electronically controlled ankle joint in which the angle of foot springs about an ankle joint is altered by means of a motorised coupling.

It is an object of the present invention to provide a more natural function in a variety of situations.

SUMMARY OF THE INVENTION

According to a first aspect of the present invention, a prosthetic ankle and foot combination comprises a foot component and an ankle joint mechanism, the ankle joint mechanism including a shin component and being constructed to allow damped rotational movement of the foot component relative to the shin component about a medial-lateral joint flexion axis, wherein: the ankle joint mechanism is arranged to provide a continuous hydraulically damped range of ankle motion during walking with dynamically variable damping resistances associated with ankle motion in the plantar-flexion and dorsi-flexion directions respectively; the combination further comprises a control system coupled to the ankle joint mechanism having at least one sensor for generating signals indicative of a kinetic and/or kinematic parameter of locomotion and/or walking environment; and the ankle joint mechanism and the control system are arranged such that the damping resistances effective over the said range of motion and associated with motion in the plantar-flexion and dorsi-flexion directions are adapted automatically in response to the said signals. Preferably, the damping resistance is the predominant resistance to ankle joint flexion over at least part of the said range of ankle motion.

Advantageously, the control system is programmed to generate signal indicative of terrain, e.g. ground inclination, and to vary the degree of damping resistance in the direction of both ankle dorsi-flexion and ankle plantar-flexion. Particular benefits are achieved if the damping resistance in the direction of plantar-flexion is automatically decreased when the control system generates signals indicative of walking down an incline and increased when indicative of walking up an incline, compared with a level of resistance in that direction set for walking on the level. Conversely, it is preferable that the control system operates such that the damping resistance in the direction of dorsi-flexion is increased compared with the level walking resistance level in the dorsi-flexion direction when the control system signals are indicative of walking down an incline and decreased when the signals are indicative of walking up an incline.

The control system may also be capable of detecting walking on stairs as another kind of terrain variation. In such a case, the damping resistance may also be automatically adjusted in response to signals generated by the control system, the resistance in the direction of plantar-flexion being decreased when the signals are indicative of walking upstairs and increased when the signals are indicative of walking downstairs.

Another parameter that may be used for altering damping resistance is walking speed (or step period or its reciprocal step rate, commonly referred to as "cadence"). As the speed of walking or cadence value increases, the control system preferably decreases the resistance of the hydraulic damping in the direction of dorsi-flexion. Conversely, when the user is walking more slowly, the resistance in the direction of dorsi-flexion is increased. In addition, resistance in the plantar-flexion direction is increased when walking faster and decreased when walking slower.

Various ways of indicating kinetic or kinematic parameters of locomotion may be used. One preferred sensor is an accelerometer, typically a two-axis accelerometer, mounted in the foot component. It will be appreciated that such an accelerometer can produce signals indicative of foot component inclination, as well as gait characteristics such as acceleration or deceleration at heel strike. Foot component angular velocity can also be measured by processing the sensor output in the control system to integrate the acceleration output over time. Techniques for processing output signals from an accelerometer to obtain kinetic and kinematic parameter data such as those referred to above are set out in Morris, J. W "Accelerometry—A Technique for the Measurement of Human Body Movements", Journal of Biomechanics, 1973, pages 726-736. Additional information is contained in Hayes, W. C et al. "Leg Motion Analysis During Gait by Multiaxial Accelerometry: Theoretical Foundations and Preliminary Validations", Journal of Biomechanical Engineering, 1983, vol. 105, pages 283-289. The content of these papers is incorporated in this specification by reference.

A second sensor is also, preferably, provided in the form of, for instance, a magnetic transducer sensing the relative position of the foot component and the shin component. This may be performed by direct measurement of the relative angular position or by sensing the linear displacement of one element of the ankle joint mechanism with respect to another in the case of the mechanism including, for instance, a linkage converting relative rotational movement of the foot component with respect of the shin component to relative translational movements.

Such a sensor may be used for sensing cadence (step rate) and the amplitude of ankle flexion. Measurement of the piston stroke indicates the magnitude of flexion. Changes to the signal characteristics may be used to indicate indirectly step rate, for example, the time taken to reach a particular flexion angle or, alternatively, measurement of the time taken for the ankle angular velocity to indicate a change from plantar-flexion to dorsi-flexion.

Hydraulic damping resistance is preferably introduced in the prosthesis described above by means of a joint mechanism in the form of a hydraulic piston and cylinder assembly. In the case of this being a linear piston and cylinder assembly, it is connected to an associated linkage arranged to convert between translational piston movement and rotational relative movement of the foot component and the shin component. The piston and cylinder assembly includes at least one damping control valve which is adjustable during locomotion by an actuator coupled to the valve. The valve is arranged such that, when adjusted, it varies the degree of hydraulic damping resistance to the piston movement. Independent control of damping resistance in the directions of dorsi-flexion and plantar-flexion may be achieved by having two such valves with respective associated non-return valves.

In preferred embodiments of the invention, control of the damping resistance is such that, at an angular position within at least part of the range of ankle motion, the resistance can be any of several (e.g. at least three) different levels. Indeed, the resistance is preferably continuously variable. It is possible to maintain the damping resistance, preferably in the case of both resistance to plantar-flexion and resistance to dorsi-flexion, at a set level so long as the walking characteristics indicated by the sensor or sensors of the control system do not change. This means, for instance, that a valve in a hydraulic circuit within the ankle joint mechanism can be adjusted to any of several different positions having respective different orifice areas according to signals produced by the control system and that, once the valve has been adjusted to provide a particular orifice area, no further adjustment of the valve may be needed so long as the walking characteristics or parameters indicated by the sensors do not change. This has advantages in terms of minimising power consumption. However, when power and energy limitations permit it, the damping resistance can be altered on each step such that, for example, the resistance to motion in the direction of dorsi-flexion can be increased as the angle of dorsi-flexion increases, i.e. increasing from a variable resistance level governed by signals generated in the control system in response to sensor outputs, to a higher level of resistance beyond a given dorsi-flexion angle. Different damping resistance relationships to sensed walking characteristics may be used, as follows.

The change in damping resistance may be linearly proportional to a sensed characteristic such as ground inclination or walking speed. This may apply to one or both of resistance in the direction of dorsi-flexion and resistance in the direction of plantar-flexion.

The change in damping resistance may follow a predetermined non-linear function (e.g. according to a square law or other polynomial) with respect to the sensed characteristic.

Changes in ground inclination may be sensed indirectly by measuring a gait characteristic such as the timing or duration or specific gait events or phases, e.g. the time taken for the foot to reach a flat-foot state or to stop plantar flexing after heel-strike. In such a case, the resistance to movement in the direction of plantar-flexion may be adjusted to prevent the duration of plantar-flexion exceeding a predetermined maximum. In particular, the maximum plantar-flexion duration allowed is never greater or less than a predefined or programmable time, depending on walking requirements.

The change in damping resistance may also be governed as a function of a gait measurement such as the acceleration recorded at heel-strike. In such a case, the resistance in the direction of plantar-flexion is adjusted to limit the maximum acceleration occurring during the loading response phase of gait to a predetermined or programmed value.

Changes in damping resistance may be determined from a function which is a combination of measured gait characteristics such as walking speed, cadence, surface inclination, stride-length and changes in step height (e.g. up or down a step) or any another kinetic or kinematic parameter measured during locomotion.

The changes in resistance in the direction of plantar-flexion and dorsi-flexion respectively may be mutually adapted, i.e. according to one another. Thus, in the case of walking down an incline, a decrease in plantar-flexion resistance compared with the value for level walking, may be automatically accompanied by an increase in dorsi-flexion resistance by a predetermined or programmable factor.

Changes in damping resistance may be specifically programmed under different trial conditions with specific parameter values, such damping resistances being stored in a memory in the control system, the system being programmed such that during normal use (i.e. during a playback phase as opposed to a teaching phase) appropriate damping resistance values are computed by interpolation between stored values when the sensed parameters lie between the parameter values used for programming.

According to another preferred scheme of operation, the control system may store a database of damping resistance settings for movement in both dorsi-flexion and plantar-flexion directions, which database is derived from clinical testing data. In this embodiment, a look-up table of settings is stored in the control system memory. The stored data is obtained from test results with a variety of users, rather than values obtained specifically for the individual user.

Depending on the provision of heel-adjustment means in the mechanism, changes in damping resistance may be derived from a calibration routine whereby the damping resistance variation is optimised according to different heel heights, the calibration being performed in the same way as surface gradient calibration.

The sensitivity of changing damping resistance in response to changing walking requirements may be defined in different ways. For instance, the changes in walking requirements may be determined on an individual step-by-step basis. Alternatively, the changes in walking requirement may be determined based on a measured average of a previous number of steps of a specific variable such as gait speed and inclination or other measured gait variable. The changes in walking requirements may be subdivided into bands defining response sensitivity. For instance, walking speed may be subdivided into cadence (step-rate) bands or ranges. Similarly, changes to ground inclination may be subdivided into bands of a few degrees at a time. The limits of such bands may be uniformly distributed over the range of the relevant parameter or characteristic, or non-uniformly. Such limits may be predetermined or programmable, or they may be continuously or step-wise self-adaptive, such adaptation being based on clinical testing with a variety of amputees or upon responses measured with an individual user. Another aspect of the invention provides a lower limb prosthesis comprising a shin component, a foot component, and a joint mechanism interconnecting the foot and shin components and arranged to allow damped pivoting of the foot component relative to the shin component about a medial-lateral joint flexion axis during use, wherein the joint mechanism comprises a hydraulic piston and cylinder assembly and an associated linkage arranged to convert between translational piston movement and rotational relative movement of the foot component and the shin component, the piston and cylinder assembly including an adjustable damping control valve arranged to vary the degree of hydraulic damping resistance to the said translational piston movement at least insofar as such movement is associated with flexion of the foot component relative to the shin component, and wherein the prosthesis further comprises a valve control system including at least one sensor for generating signals indicative of a kinetic or kinematic parameter of locomotion and, coupled to the control valve, an actuator for adjusting the valve, the control system being arranged to adjust the valve during locomotion thereby to vary the hydraulic damping resistance of the joint mechanism to flexion in response to the signals from the sensor. The invention also includes a prosthetic ankle and foot combination and a prosthetic ankle joint each having the above features.

As described above, the way in which damping resistance may be varied can be programmable so that, for instance, the control system is arranged to have a "teach" mode in which a prosthetist may select and store damping resistance settings for different speeds of walking and different terrains (e.g. ascending stairs or an incline, descending stairs or an incline, and walking on level ground), these settings being determined during test sessions with the amputee. Alternatively, a self-tuning system may be used whereby control parameters are automatically adjusted towards specific values under known walking conditions. As a further alternative, settings may be stored in a database or as a look-up table derived from clinical tests on a variety of patients, the settings having related to sensed or computed parameters. A combination of these methods may be used.

In accordance with the principle outlined above, the valve control system may be arranged to generate a signal indicative of a kinetic or kinematic parameter which varies during individual gait cycles and to drive the valve so as to increase and decrease hydraulic resistance to flexion during each of a plurality of gait cycles, the direction, magnitude and timing of such changes in resistance being dynamically adjustable during locomotion. In one embodiment the system operates such that the hydraulic resistance to dorsi-flexion is increased to a maximum value during the stance phase of the gait cycle, the time at which the maximum value is reached being altered in the stance phase, for example occurring later in the stance phase, when the signal indicative of terrain indicates walking down stairs or up an incline compared with the time at which the maximum value is reached when the said signal indicates walking on level ground.

According to another aspect of the invention, a prosthetic ankle and foot combination comprises a foot component and a hydraulic ankle joint mechanism, the ankle joint mechanism including a proximal shin component and being constructed to allow damped rotational movement of the foot component relative to the shin component about a medial-lateral joint flexion axis, wherein the ankle joint mechanism is arranged to provide (a) continuous hydraulically damped ankle flexion during walking relative to a present reference angular position of the foot component with respect to the shin component and (b) adjustment of the reference angular position. The adjustment of the reference angular position may also be damped, preferably hydraulically, and may be user adjustable. Once the reference angular position has been set, the range of rotational movement of the foot component relative to the shin component is preferably a single fixed range. Within that range or at least a major part of it, adaptive damping control is effected, the relationship between damping resistance levels being defined according to changing requirements of locomotion such as terrain (surface inclination and/or stairs, and walking speed or cadence). Within the range of rotational movement, damping resistance is preferably continuously variable or variable in a series of steps such that, typically, whilst the walking requirements remain constant, a programmed damping resistance level in a given direction (plantar-flexion, dorsi-flexion, or both) is maintained throughout the gait cycle and remains constant from step-to-step. It is also possible for dynamic damping of flexion during walking to be manually varied rather than automatically adaptively varied.

In such a combination, the mechanism preferably comprises a piston and cylinder assembly having a first piston element movable in a cylinder to drive hydraulic fluid through an orifice in response to rotation of the foot component relative to the shin component, the mechanism further comprising a first valve defining the orifice and an electrical actuator for driving the valve to vary the area of the orifice thereby to provide dynamically variable hydraulic damping of ankle flexion during walking.

The mechanism may comprise a second valve element defining another orifice through which hydraulic fluid is driven when the first piston element moves in response to rotation of the foot component relative to the shin component, the first and second valves being constructed and arranged such that the first valve and the second valve independently determine the damping resistance of the mechanism to flexion in the dorsi-flexion and plantar-flexion directions respectively.

The damped adjustment of the reference angular position may be performed by arranging for the mechanism to comprise further a second piston element and a locking valve, wherein the second piston element is arranged to drive hydraulic fluid through the locking valve in response to rotation of the foot component relative to the shin component, and the locking valve can be closed to lock the second piston element thereby to set the reference angular position of the foot component with respect to the shin component.

Accordingly, in one preferred embodiment, the ankle joint mechanism comprises a hydraulic piston and cylinder assembly and an associated linkage arranged to convert between translational piston movement and rotational relative movement of the shin component and the foot component; the piston and cylinder assembly comprises first and second piston elements which are substantially coaxial and substantially aligned with the shin axis; the first piston element has a neutral position in the assembly and is located in a cylinder so as to drive hydraulic fluid through an orifice when moved from the neutral position in response to pivoting of the foot component from a preset reference angular position relative to the shin component, the fluid flow through the orifice damping the said pivoting; and the second piston element is arranged to drive hydraulic fluid through a locking valve in response to pivoting of the foot component relative to the shin component, which valve can be closed to lock the second piston element thereby to set the said reference angular position corresponding to the neutral position of the first piston element. In this way it is possible to allow dorsi-plantar-flexion of the ankle over a limited range of movement with largely damped, as opposed to resilient, resistance to motion, resulting in an ankle which is able easily to flex under load according to changing activity requirements without generation of high reaction moments which would otherwise cause discomfort and compromise the function of the prosthesis.

The position of the foot component relative to the shin component at a given position of the first piston element may be independently adjusted by opening the normally closed locking valve and causing the second piston element to move in the assembly until a required relative orientation of the foot component and the shin component is reached, whereupon the locking valve is closed again. The "given position" of the first piston element is referred to above as the neutral position. Although this so-called neutral position may be defined by resilient elements in the mechanism biasing the first piston element towards a particular position in the cylinder, the "neutral" position may be notional in the sense that it is not defined by any characteristic or feature of the piston and cylinder assembly as such, but may be merely a position selected by the user or prosthetist for the purpose of setting the reference angular position by adjusting the position of the second piston element.

Preferably an interlocking device is provided to lock the first piston element whilst this adjustment is being made. This adjustment allows control of dorsi- and/or plantar-flexion of the ankle to be performed with reference to a selected reference angular position of the foot component and the shin component, this reference orientation of one component relative to the other being selected according to, e.g., shoe heel-height or to achieve particular functional characteristics required by the user's prosthetist. It will be noted that the ability to set the reference angular position independently of the damping function, and without moving the first piston element, has the effect of maintaining the effective range of dorsi- and/or plantar-flexion of the ankle during use of the prosthesis irrespective of shoe heel-height.

The piston and cylinder assembly can be constructed in a number of different ways. In one embodiment of the invention, one of the piston elements is slidable in a bore formed in the other piston element. One of the piston elements may form a transversely extending movable wall of a chamber which houses the other piston element.

In the case of one piston element being slidable in a bore formed in the other, the former element may comprise two pistons interconnected by a piston rod which slides in the bore as well as being slidable within the cylinder referred to above. The space between the two pistons contains a dividing wall dividing the space into two variable volume chambers interconnected by a first passage containing a valve element. This valve element is typically drivable over a range of positions by a servo motor or a stepper motor under electronic control in order to vary the area of the orifice and, therefore, the resistance to movement of the first piston element and, consequently, rotation of the ankle joint during use (i.e. during locomotion, whether it be walking, running, climbing or descending ramps and stairs, and so on). Such an arrangement may be duplicated, albeit with oppositely directed respective non-return valves as well, for servo or stepper motor controlled damping resistances independently for the directions of dorsi-flexion and plantar-flexion, as will be described in more detail below.

In this preferred embodiment, the so-called "other" piston element constitutes at least part of the dividing wall, both piston elements being slidable within a common cylinder. Conveniently, both piston elements are dual piston components, each having two pistons interconnected by a respective piston rod, the cylinder being a transverse wall dividing the space between the two pistons of the piston element having the above-mentioned internal bore. This transverse wall contains a valved second passage linking the chambers formed on opposite sides of the transverse wall. It is preferably this second passage with which the locking valve is associated, the first passage or passages containing the damping orifice.

Alternatively, as in another embodiment of the invention, the piston and cylinder assembly comprises two cylinder units which are pivotally interconnected and which house the first and second piston elements respectively. The piston element in one of the cylinder units is pivotally connected to the other cylinder unit such that its movement is associated with pivoting of one cylinder unit with respect to the other. This other cylinder unit, and the piston element housed in it, are pivotally connected to either the foot component or the shin component such that movement of the respective piston element is associated with pivoting of the other cylinder unit with respect to the foot or shin component to which is it pivotally connected. Where the above-mentioned other cylinder unit is pivotally connected to the foot component, the first mentioned cylinder unit forms part of the shin component, and vice-versa. In effect, the piston and cylinder assembly comprises two cylinder units stacked one above the other, operation of one being associated with relative pivoting of the shin component and an intermediate component and operation of the other being associated with relative pivoting of the intermediate component and the foot component. Preferably, the cylinder unit which is located proximally, i.e. forming part of or attached to the shin component, contains the locking valve and is, therefore, used for setting the reference angular position, whilst the other cylinder unit, located so as to be connected to the foot component, serves to perform ankle joint damping. It is, however, possible to reverse the positions of the cylinder units. In any of the above embodiments, the piston and cylinder assembly may include a valve element operable to prevent fluid flow through the damping orifice. The above-mentioned interlocking device operates to prevent simultaneous opening of the valve element and the locking valve.

Advantageously, the interlocking device forms part of an electronic valve control system including electrical actuators for the locking valve and the above-mentioned valve element, the control system being configured to constrain operation of the actuators such that, at least in normal circumstances, either the locking valve or the dynamically adjustable valve element is in its closed condition at any given time. The valve element may, itself, be part of a damping control valve defining the damping orifice, the valve control system including a transducer or sensor adapted to produce an electrical signal indicative of walking speed or terrain, the control system having a first output coupled to the damping control valve actuator and being arranged to produce at such output an actuator drive signal which causes the damping control valve to vary the orifice area according to the indicated parameter or parameters.

The preferred valve control system has a second output coupled to an electrical actuator for the locking valve, which may be a servo motor or a solenoid, so that the valve control system can be used to open or close the locking valve depending on whether a dynamic response mode or a setting mode is selected. In the dynamic response mode, actuator drive signals are produced at the first and second outputs to cause the damping control valve to be open to a degree depending on terrain and walking speed, and the locking valve to be closed. Conversely, in the setting mode, the actuator drive signals cause the damping control valve to close and the locking valve to open to allow setting of the said reference angular position of the foot component relative to the shin component.

In other variants of the invention, differential control of the resistance to flexion in the dorsi direction and plantar direction respectively may be provided using, for instance, two damping control valves in respective passages which function in parallel, i.e. one allowing the flow of fluid in one direction from a variable volume chamber which varies in size with movement of the first piston element, and the other allowing the flow of fluid in the opposite direction to the variable volume chamber. Non-return valves may be used to define the direction of flow in each case. Separate electrical actuators may be provided for each damping control valve to allow dynamic variation of resistance to flexion in each direction. Alternatively, one or both may be manually pre-settable. It is particularly preferred that the valve control system is adapted such that the actuator drive signal fed to the output control valve actuator for dorsi-flexion damping control causes the damping control valve to increase the orifice area as the indicated walking speed increases, thereby decreasing dorsi-flexion damping resistance with increasing walking speed and vice-versa.

The invention also includes a prosthetic ankle and foot combination comprising a foot component and an ankle joint mechanism, which mechanism includes a proximal mounting interface, the joint mechanism being arranged to allow limited damped pivoting of the foot component relative to the mounting interface about a medial-lateral joint flexion axis during use, wherein: the mechanism comprises a hydraulic piston and cylinder assembly and an associated linkage arranged to convert between translational piston movement and rotational relative movement of the proximal mounting interface and the foot component; the piston and cylinder assembly comprises first and second piston elements which are substantially coaxial and substantially aligned with the shin axis; the first piston element has a neutral position in the assembly and is located in a cylinder so as to drive hydraulic fluid through an orifice when moved from the neutral position in response to pivoting of the foot component from a preset reference angular position relative to the proximal mounting interface, the fluid flow through the orifice damping the said pivoting; and the second piston element is arranged to drive by hydraulic fluid through a locking valve in response to pivoting of the foot component relative to the proximal mounting interface, which valve can be closed to lock the second piston element thereby to set the said reference angular position corresponding to the neutral position of the first piston element. As an alternative to setting the reference angular position via a hydraulic device, other mechanical adjustment devices may be used to adjust the position of the ankle interface (pyramid device or shin clamp) to accommodate changes to heel height.

According to yet a further aspect of the invention, a prosthetic ankle joint assembly comprises a proximal mounting interface, a distal mounting interface, and a joint mechanism interconnecting the proximal and distal mounting interfaces and constructed to allow damped rotational movement of the proximal mounting interface relative to the distal mounting interface about a medial-lateral joint flexion axis during use, wherein the joint mechanism is arranged to provide a continuous hydraulically damped range of ankle motion during walking with dynamically variable damping resistances associated with ankle motion in the plantar-flexion and dorsi-flexion directions respectively; the ankle joint assembly further comprises a control system coupled to the joint mechanism having at least one sensor for generating signals indicative of a kinetic and/or kinematic parameter of locomotion; and the joint mechanism and the control system are arranged such that the damping resistances effective over the said range of motion and associated with motion in the plantar-flexion and dorsi-flexion directions are adapted automatically in response to the said signals.

The invention also includes a lower limb prosthesis including a prosthetic ankle and foot combination as defined above.

Independent control of plantar-flexion damping resistance assists knee stability in above-knee amputee locomotion by managing the ground reaction vector orientation with respect to the knee joint centre specifically to diminish the flexion moment about the knee. This function is useful when for example walking down a ramp; a lower level of resistance to plantar-flexion allows the foot to realign to the walking surface without generating substantial reaction moments which would otherwise cause the knee to become unstable.

According to yet a further variant, a lower limb prosthesis comprises a shin component, a foot component, a joint mechanism interconnecting the foot and shin components and arranged to allow limited damped pivoting of the foot component relative to the shin component about a medial-lateral flexion axis during locomotion, and a control system having at least one sensor for generating signals indicative of at least one characteristic of locomotion, the joint mechanism including a device for adjusting, the limit of dorsi-flexion of the foot component relative to the shin component during locomotion. Typically the control system is arranged to generate signals indicative of walking on stairs or on an incline and to alter the dorsi-flexion limit to increase the maximum degree of dorsi-flexion permitted by the joint mechanism when such signals are produced compared with the degree of dorsi-flexion permitted by the adjusting device when signals are generated indicative of walking on level ground. A further adjusting device may be included for adjusting the degree of damping resistance of the joint mechanism in the directions of dorsi-flexion and plantar-flexion respectively in response to signals from the control system, the control system and the joint mechanism being arranged such that the dorsi-flexion limit and the damping resistances are independently adjustable during locomotion.

Again, it should be noted that features set out above in relation to a lower limb prosthesis may also, according to the invention, be provided in a prosthetic ankle-foot combination or in a prosthetic ankle joint having proximal and distal mounting interfaces for shin and foot components respectively.

The invention will be described below by way of example with reference to the drawings.

IN THE DRAWINGS

FIGS. 13A to 13D are graphs illustrating the variation of damping resistances according to walking surface inclination and walking speed.

DETAILED DESCRIPTION OF THE INVENTION

Figure 1:
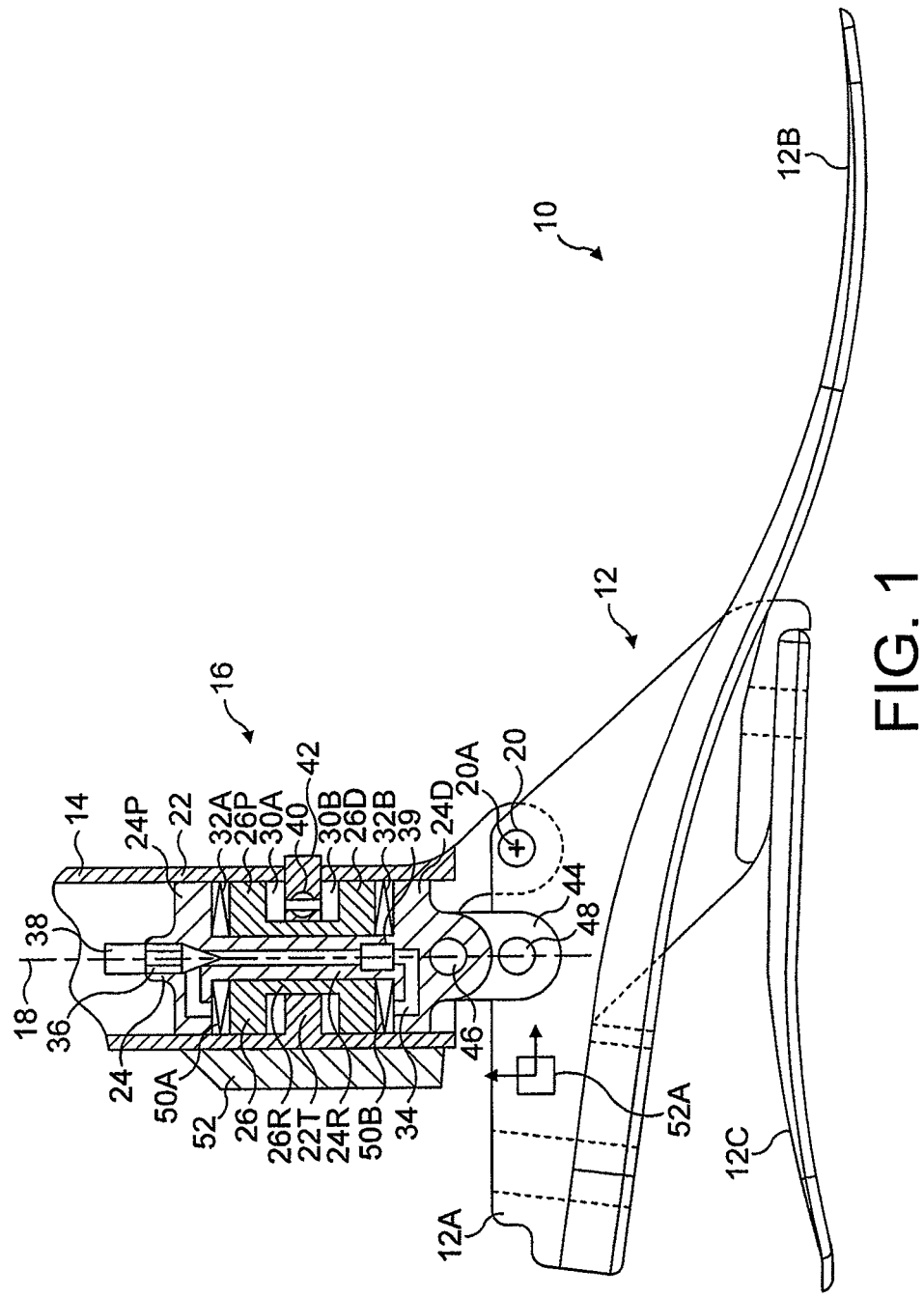
FIG. 1 is a sectional view of a lower limb prosthesis incorporating a first ankle and foot combination in accordance with the invention.

Referring to FIG. 1, a lower limb prosthesis in accordance with the invention has a foot component 10 with a foot keel 12 comprising a rigid carrier 12A. Independently coupled to the rigid carrier 12A are a toe spring 12B and a heel spring 12C. The keel 12 is largely formed from carbon fibre composite material and can be surrounded by a foam cosmetic covering (not shown).

Coupled to the foot keel 12 is a shin component 14 having, at its distal end, an ankle joint mechanism 16 which is housed largely within the shin component 14 and connects the shin component 14 to the foot keel 12. The shin component 14 defines a shin axis 18. The mounting of the shin component 14 to the foot keel 12 is by way of an ankle flexion pivot 20 defining a flexion axis 20A running in a medial-lateral direction to the anterior of the shin axis 18. The ankle joint mechanism is in the form of a piston and cylinder assembly, the cylinder 22 of which forms an extension of a shin tube centred on the shin axis 18. The cylinder 22 slidably houses two coaxial piston elements 24, 26, the axes of which, in this case, coincide with the shin axis 18. These two piston elements comprise a first piston element 24 for providing a dynamic damping action during locomotion, and a second piston element 26 for independent adjustment of heel-height. As will be understood from the description which follows, these two piston elements are able to move translationally in the cylinder 22 independently of each other so that a heel-height setting can be established without affecting the function of dynamic damping action provided by the first piston element.

To describe the piston and cylinder assembly in more detail, the dynamic piston element 24 has two pistons 24P, 24D interconnected by an axial piston rod 24R. Located in the space between the two pistons 24P, 24D, the second piston element 26, for heel-height adjustment, is also reciprocable within the cylinder in the space between the pistons 24P, 24D of the first piston element and, itself, has two spaced, apart pistons, 26P, 26D which are interconnected by a respective piston rod 26R. The heel-height adjustment piston 26 has an axial bore running its entire axial length to house the piston rod 24R of the dynamic damping piston element 24. Between the pistons 26P, 26D of the heel-height adjustment piston element 26 is a transversely extending dividing wall 28 which is fixed to the inside of, or is integral with, the cylinder 22, thereby dividing the space between the two pistons of the second piston element 26 into two annular variable-volume chambers 30A, 30B.

The axial extent of the second piston element 26 is such that a further two annular variable-volume chambers 32A, 32B are created between, respectively, the two proximal pistons 24P, 26P of the piston elements 24, 26 and between the two distal pistons 24D, 26D of the two piston elements 24, 26.

Both pairs of annular variable-volume chambers 30A, 30B; 32A, 32B are filled with hydraulic fluid.

Running through the body of the dynamic damping piston 24 so as to interconnect the two annular chambers formed between this piston element and the heel-height adjusting piston element 26 are two passages 34 arranged in parallel, each with a damping control valve 36. (Only one passage and one such control valve is shown in FIG. 1.) Valves 36 are each in the form of a tapered valve element threaded in the body of the dynamic damping piston element 24 and driven by a respective electrical actuator in the form of a servo motor 38 to allow variation in the area of the orifice created by the penetration of the valve element of the valve 36 into the passage 34. (Again, only one servo motor 38 appears in FIG. 1.) It will be appreciated that operation of the servo motors 38 varies the resistance to fluid flow between the outer annular chambers 32A, 32B and hence the resistance to movement of the first piston element 34 with respect to the second piston element 26. Non-return valves 39 (one of which is shown in FIG. 1) located in the passage 34 confine fluid flow in the respective passages to flow in response to dorsi-flexion and plantar-flexion of the ankle joint so that the orifice area of one valve 36 governs the damping resistance in the direction of dorsi-flexion and that of the other valve 36 governs resistance in the direction of the plantar-flexion.

A third valve, for heel-height adjustment and in the form of a locking valve 40, is housed in the transverse wall 22T to interconnect the two inner annular chambers 30A, 30B. This valve is operated by a third electrical actuator 42 and can be opened or closed to allow movement or prevent movement of the second piston element 26 in the cylinder 22 respectively.

The translational movement of the piston elements 24, 26 is associated with pivotal movement of the foot component 10 relative to the shin component 14 about the shin connection axis 20A. This occurs by virtue of the axis 20A being offset from the shin axis 18, and a pivotal connection and a connecting link 42, 44 between interconnecting the dynamic damping piston element 24 at its distal end and the foot keel 12, the link having pivotal connections to each of these two components. Since the pivotal connection axis 20A and the axis of the lower pivotal connection 48 of the link 44 are spaced apart laterally with respect to the axis of the piston elements 24, 26, rotational forces acting upon the prosthetic foot 10 are translated to linear axial forces on the piston elements 24, 26.

In this embodiment of the invention, there are springs 50A, 50B in the outer annular chambers 32A, 32B biasing the dynamic damping piston element 24 to a neutral position with respect to the heel-height adjustment piston element 26. The springs 50A, 50B are optional. The neutral position is not defined by the springs 50A, 50B but, rather, is a notional datum with respect to the second piston element 26, in this embodiment, for the purpose of adjusting the position of the heel-height adjustment piston element 26.

Control of the electrical actuators 38, 42 is performed by a valve control system 52 which has a first sensor 52A mounted on the keel 12 of the foot component 10 and a second sensor (not shown) within the casing of the main part of the control system 52. The first sensor 52A is a dual-axis accelerometer having outputs indicative of acceleration of the foot component both parallel to and perpendicular to the shin axis 18. The second sensor is a magnetic transducer located to sense the positions of the piston elements 24, 26 in the cylinder 22. The functions of the valve control system include (a) providing an electrical interlock between the actuators 38, 42 for the valves 36, 40 in order that only the pair of damping valves 36 or the locking valve 40 is open to prevent them being simultaneously open and (b) to adjust the orifice area determined by the valve 36 dynamically i.e. in real-time during locomotion in response to kinetic or kinematic parameters of locomotion as sensed by the sensors forming part of the control system 52.

Figure 2:
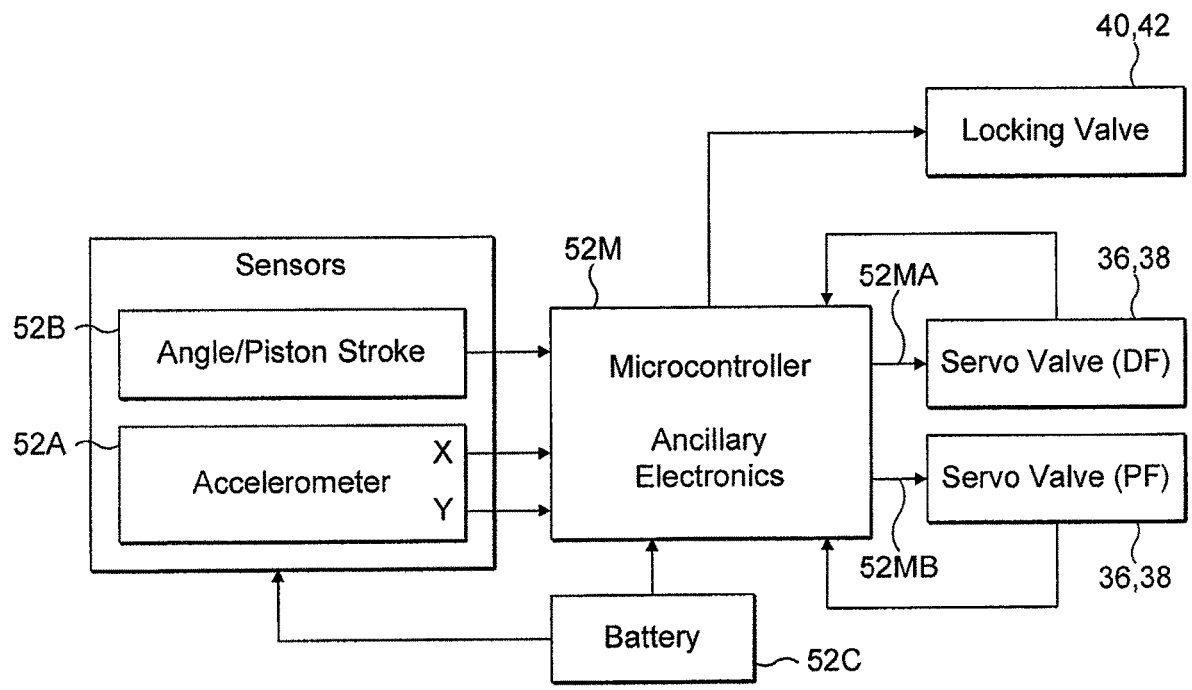
FIG. 2 is a block diagram of a control system forming part of the prosthesis of FIG. 1, shown connected to a pair of servo valves for controlling damping resistance.
Figure 3:
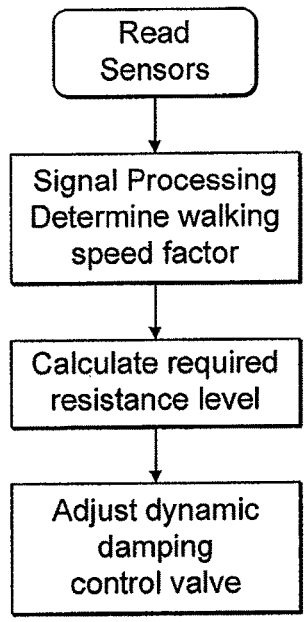
FIG. 3 is a flow diagram for dynamic damping control.

The latter function of the control system 52 is indicated diagrammatically in FIGS. 2 and 3 insofar as signals derived from the sensors 52A, 52B within the valve control system 52 are fed to a microprocessor control unit 52M which processes the received signals to provide indications of surface inclination and walking speed, specifically determining an "inclination factor" and a "walking speed factor". The microprocessor calculates a required resistance level in the form of valve positions for the control valves 36 and provides corresponding output signals on first and second outputs 52MA, 52MB of the control unit 52M to the actuators 38 for the dynamic damping control valves 36 to drive their valve elements to the required positions.

The programming of the microprocessor unit 52M is such that the valve controlling resistance to rotation in the direction of dorsi-flexion is driven towards its open position as the indicated walking speed increases or when an upwardly inclined surface is indicated, and towards its closed position when the indicated speed decreases or when a downwardly inclined surface is indicated (i.e. in order that the resistance to flexion of the ankle is decreased at higher walking speeds and when walking up an incline).

In a similar manner, the microprocessor causes the valve that controls resistance to rotation in the direction of plantar-flexion to move towards its open position as the indicated walking speed decreases or when a downwardly inclined surface is indicated, and to move towards its closed position when the indicated speed increases or when an upwardly inclined surface is indicated (i.e. in order that the resistance to flexion of the ankle is decreased at slower walking speeds and when walking down an incline).

Operation of the ankle joint mechanism for the purpose of heel-height adjustment will now be described in more detail. It will be understood that the inner piston element, i.e. the heel-height adjustment piston element 26, acts as a movable mechanical reference which can be adjusted to compensate for changes in heel-height. The locking valve 40 is normally set locked so that the inner piston element 26 is locked with respect to the cylinder 22. This is the situation during the so-called "dynamic response" mode of the valve control system, the dynamic damping control valve 36 being operated as described above during this mode. In a second mode of the valve control system, a "heel-height setting" mode, the dynamic damping control valve 36 is driven to its fully closed position thereby locking the outer piston element 24, i.e. the dynamic damping piston element, with respect to the inner piston element 26 so that the other moves in concert with it. In other words, the spacing between the two piston elements 24, 26 is fixed. During the heel-height setting mode, the locking valve 40 is driven to its open position, allowing the inner piston element 26 to move in the cylinder 22 in response to rotational forces applied to the foot 10. In this way, providing the damping piston element 24 is set to a predetermined position with respect to the heel-height adjustment piston element 26 beforehand, the foot 10 can be set to a required angle with respect to the shin component 14, whereupon the valve 40 is closed and normal operation of the valve control system in the dynamic response mode can be resumed.

Figure 4:
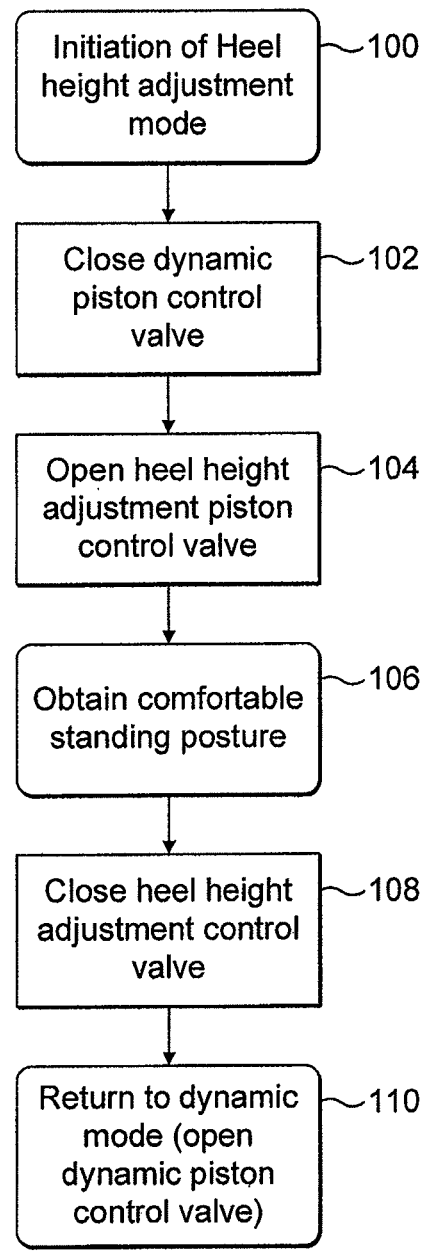
FIG. 4 is a flow diagram for heel-height adjustment.

Referring to FIG. 4, therefore, heel-height adjustment includes the following steps executed by software controlling the microprocessor in the valve control system 52. Firstly, the heel-height adjustment mode is initiated (step 100), then the damping control valves 36 are driven to their closed position (step 102), after which the locking valve 40 is driven to its open position (step 104). At this point, the user is instructed to adopt a comfortable standing posture whilst wearing the required shoe (step 106). This causes the heel-height adjustment piston element 26 to be driven to a new set position, whereupon the locking valve 40 is driven to its closed position (step 108) and the control system 52 reverts to its dynamic response mode (step 110).

In the above way, the required range of motion during locomotion and the resistance to flexion during locomotion are maintained irrespective of the heel-height setting. Consistency in the dynamic behaviour of the prosthesis in terms of its behaviour with changing walking activities such as walking up or down inclines, on stairs, and walking at different speeds, as well as the behaviour of the system when the user is standing, is maintained. Adjustment errors are avoided by the interlocking function referred to above.

Although springs 50A, 50B are shown in FIG. 1, biasing the damping control piston element 24 to a particular position with respect to the mechanical reference provided by the heel-height adjustment piston element 26, it is preferred that such springs exert relatively small forces or, indeed, are omitted altogether so that the ankle joint mechanism provides a substantially inelastic yield over its dynamic range of flexion.

It will be noted that by separating the functions of heel-height adjustment and dynamic damping control, it is possible to maintain the damping control valves 36 in a set position so long as the walking characteristics indicated by the sensors 52A, 52B of the valve control system 52 do not change. This means, for instance, that while the user is walking at a constant speed and on a constant gradient, no battery power is required to alter the valves 36. Power is only consumed by the actuators for the valves 36 when the walking speed or gradient changes.

Figure 5:
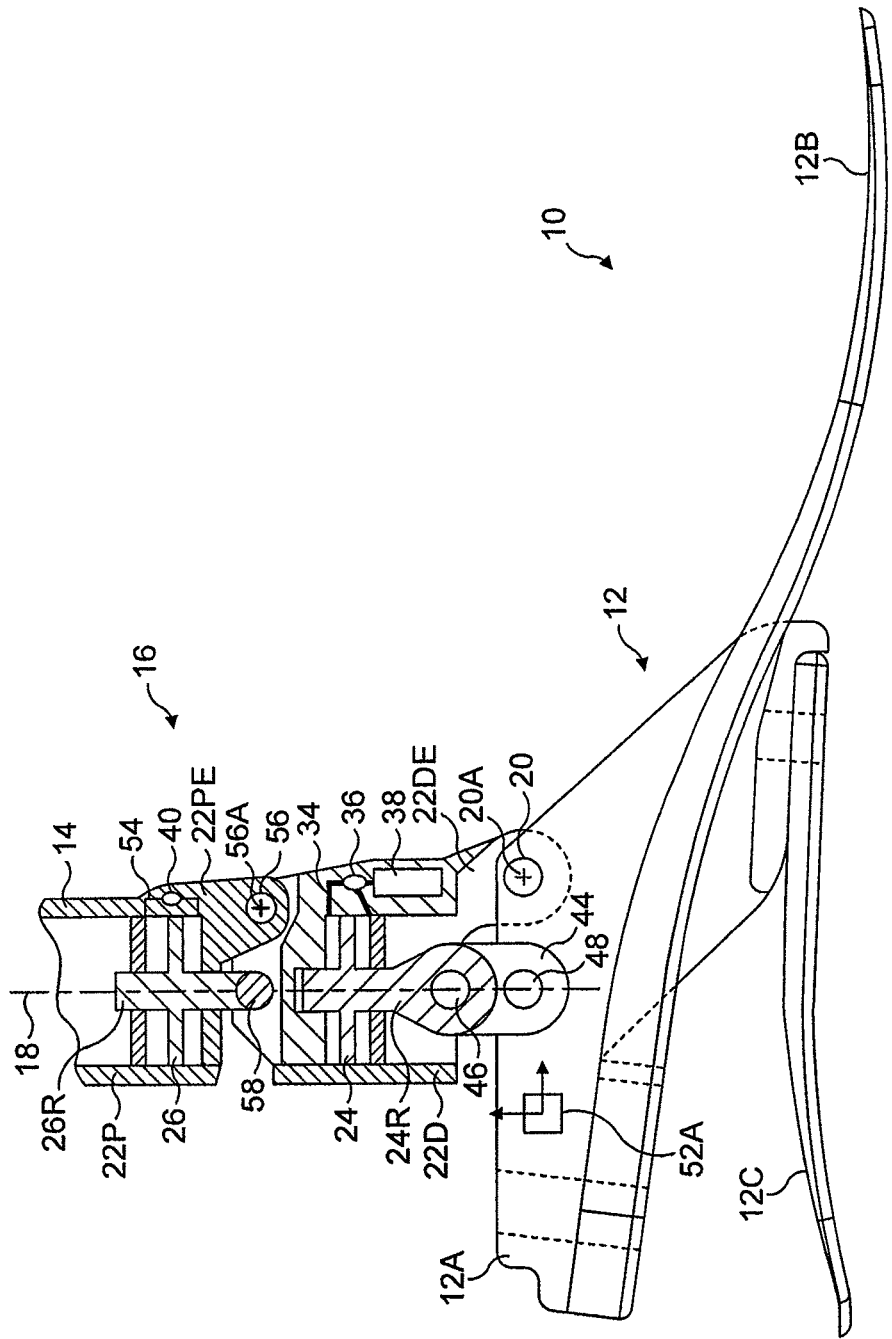
FIG. 5 is a sectional view of a lower limb prosthesis incorporating a second ankle and foot combination in accordance with the invention.

Referring, now, to FIG. 5, a second lower limb prosthesis in accordance with the invention has stacked proximal and distal cylinder units 22P, 22D. Each piston element 26, 24 in this example has a single piston on a respective piston rod 26R, 24R, each piston being independently movable within its own fluid-filled cavity in the respective cylinder unit 22P, 22D. Each piston divides its cavity into two variable-volume chambers which are interconnected with a respective passage 54, 34, each passage containing a respective valve 40, 36. In this case only one dynamic damping control valve 36 is present. At least one of the valves has an electrical actuator 38 housed on the wall of the respective cylinder unit 22D.

The distal cylinder unit 22D has anterior extension 22DE housing a pivot axial 20 for pivotally connecting the cylinder unit 22D to the prosthetic foot keel 12, the pivotal connection defining a medial-lateral connection axis 20A. As in the embodiment described above with reference to FIG. 1, a link member 44 pivotally interconnects the piston rod of one of the piston elements 24 to the foot keel at a location spaced from the pivotal connection axis 20A so that movement of the respective piston element 24 in its cylinder unit 22D is associated with rotational movement of the foot component 10 with respect to the shin about the pivotal connection axis 20A.

In this embodiment, a similar pivotal connection exists between the shin component 14, of which the proximal cylinder unit 22P is an extension, and the distal cylinder unit 22D. Again, the respective cylinder unit 22P has an anterior extension 22PE housing a pivot axle 56 to define a second pivotal connection axis 56A. Posteriorly spaced with respect to the second pivotal connection axis 56A is a pivotal connection 58 between the piston rod 26R of the piston 26 housed in the proximal cylinder unit 22P so that motion of the piston element 26 in the cylinder unit 22P is associated with pivotal movement between the proximal and distal cylinder units 22P, 22D.

In the illustrated prosthesis, the distal cylinder unit 22D and its associated piston element 24 perform flexion damping, the orifice area associated with the interconnecting passage 34 being controlled proportionally as in the first-described embodiment, using a needle valve 36 and servo motor 38. The other cylinder unit 22P and its piston element 26, together with associated locking valve 40, perform heel-height adjustment, the locking valve 40 being closed during normal operation, i.e. during the dynamic response mode.

As in the first-described embodiment, the damping control valve 36 is driven to its closed position during a heel-height adjustment mode of the valve control system.

Functioning of the ankle joint mechanism is largely the same as described above in connection with the embodiment of FIG. 1, with reference to FIGS. 2 to 4, the main differences being that only the resistance to dorsi-flexion is dynamically variable and that the pivot axis 20A is a dynamic flexion axis only rather than an axis serving for both dynamic flexion and heel-height adjustment. Instead, in this second embodiment, there is a separate heel-height adjustment axis 56A. One particular feature that this embodiment has in common with the first embodiment is that movement of the two pistons is cumulative in terms of the associated pivoting movement of the foot component with respect to the shin component 14.

Another feature which the two embodiments have in common is that the axes of the two piston elements 24, 26 are at least approximately coincident, both with each other and with the shin axis 18. Minor deviations from this rule occur in the case of the embodiment described above with reference to FIG. 5 insofar as some limiting pivoting occurs between the axis of the proximal and distal cylinder units 22P, 22D according to the set heel-height. The longitudinal orientation of the piston axes and, with both running at least approximately along the shin axis, results in a particularly compact arrangement, allowing sufficient space around the ankle joint mechanism for an ankle cosmesis that maintains a required shape.

Although each embodiment of the invention described above is a lower limb prosthesis including a shin component 14, an ankle joint mechanism 16 and a foot component 10, it will be understood that the invention also includes detachable units such as a prosthetic ankle and foot combination or a prosthetic ankle joint, the first having a shin component attachment interface on the ankle joint mechanism, and the latter having both a shin component attachment interface and a foot component interface attachment on the ankle joint mechanism. This modular approach allows the interconnection of different shin and/or foot components with the ankle joint mechanism.

Summarising, it will be seen that, in each of the above-described prostheses, at least one piston is being used to alter alignment when the prosthesis is not being used for locomotion activities, the alignment preferably being controlled electronically to reduce the risk of incorrect adjustment. A second piston, preferably under microprocessor control, is used to adapt damping characteristics of the prosthesis by way of a variable yielding action in real-time according to changing walking conditions, in particular walking speed and surface inclination. Although electronically controlled valves have been disclosed above, the valves may be manually manipulated or adjusted. Linked valve control means ensure, preferably, that the dynamic control valve is closed and not allowed to open when the heel-height adjustment valve is open.

Figure 6:
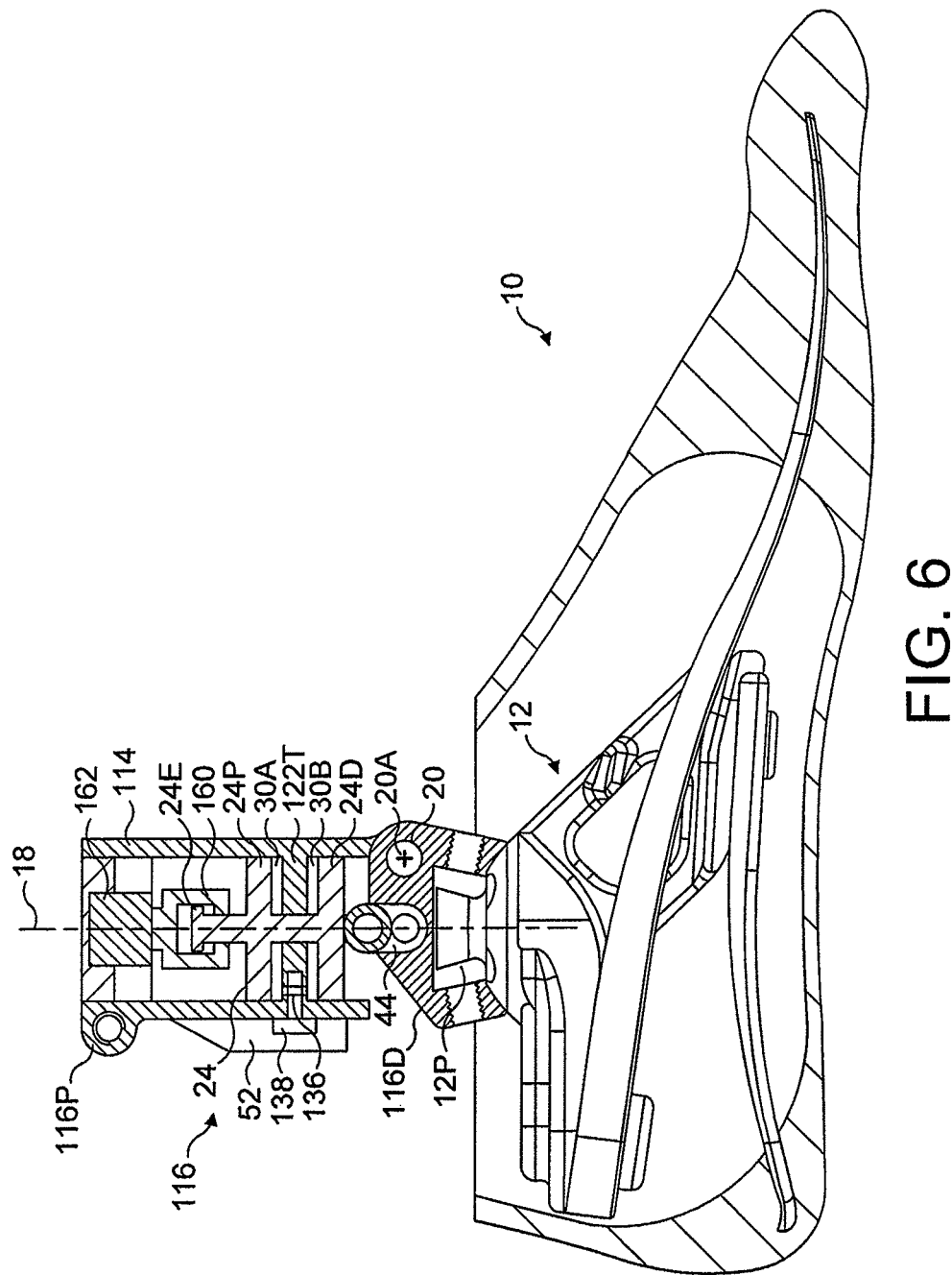
FIG. 6 is a sectional view of a third ankle and foot combination in accordance with the invention.

Dynamic valve control may be used in both single and double piston embodiments of the invention. Referring to FIG. 6, a third prosthesis in accordance with the invention is in the form of a prosthetic ankle joint 116 having proximal and distal mounting interfaces 116P, 116D, the former being in the form of a shin tube clamp defining a shin axis 18 and the latter being in the form of a conventional pyramid socket. The pyramid socket 116D receives a pyramid component 12P attached to a keel part 12 of a prosthetic foot 10. The shin tube clamp 116P forms part of a cylindrical housing 114. The housing 114 is mounted to the pyramid socket 116D by way of an ankle flexion pivot 20 defining a flexion axis 20A running in a medial-lateral direction to the anterior to the shin axis 18, as in the embodiments described above with reference to FIGS. 1 and 5. Within the cylindrical housing 114 is a single piston element 124 for providing a dynamic damping action during locomotion, the housing 114 having a transverse wall 122T separating the space between the pistons 24P, 24D of the piston element 24 into two fluid-filled chambers 30A, 30B. Transverse wall 122T includes a valve 136 with an associated electrical actuator 138, the valve and actuator acting together to vary the resistance to fluid flow between the chambers 30A, 30B as the piston 24 is moved translationally in the housing 114 in response to flexion of the foot 10 about the pivot axis 20A, such pivoting movement being converted to translational movement of the piston by the link 44 and the pivot 20.

Associated with a proximal extension 24E of the piston 24 is a piston-stroke range control collar 160. The axial position of this collar 160 is adjustable in response to operation of a linear electro-mechanical actuator 162 fixed to the housing 114. The collar 160 is shaped to provide at least a dorsi-flexion end-stop for the piston 24, thereby limiting the dorsi-flexion of the foot component 10 relative to the housing 114.

As in the previously described embodiments, an electronic control system 52 is mounted to the housing 114. This contains not only a sensor for sensing the position of the piston 24, but also, e.g., a gyroscope sensor for sensing the angular velocity of the housing 114 (and hence that of a shin tube in the shin tube connector 116P), as well as, optionally, an accelerometer or an inclinometer for measuring acceleration and angular position respectively. As before, the control system 52 includes a microprocessor for evaluating the signals from the sensors to generate signals indicative of not only speed of locomotion and surface inclination, but also terrain variation in the form of stairs, and whether the amputee is climbing or descending such stairs. The period and magnitude of signal quantities between gait events and their occurring sequences can be used for identification of speed and activity or terrain. Known motion tracking techniques, including those published in the Morris and Hayes et al papers referred to hereinabove, may also be used to determine the gradient of a walking incline and step-height differentials indicating stair walking.

The microprocessor system forming part of the control system 52 processes the signals from the sensors to adjust the two dynamic control valves 136 and the piston-stroke range control collar 160 by driving actuators 138, 162 during locomotion thereby to dynamically adjust dorsi-flexion and plantar-flexion damping resistances and flexion range, in particular to dynamically adjust the dorsi-flexion end stop. It will be noted that independent control of damping resistances and end-stop is possible.

Adjustments are performed by the control system 52 actively to adjust hydraulic stiffness and range of motion to optimise locomotion continuously when walking at various speeds and on ramps and stairs. The piston-stroke range control effectively controls the timing and quantity of energy absorption and storage in the gait cycle, whilst the valves 136 determine the rate of energy dissipation. The linear actuator 162 may be used to restrict piston travel in a manner independently from the damping valves 136 with the advantage that the actuated range control collar 160 need not be moved on every step, thereby considerably reducing the time that the control actuators are powered.

Dorsi-flexion damping resistance may be controlled separately from plantar-flexion damping resistance. Dorsi-flexion resistance is decreased with higher speeds of locomotion. In this embodiment, plantar-flexion resistance is increased with speed of locomotion. With regard to the adjustable dorsi-flexion end-stop provided by the range control collar 160 and its associated actuator 162, the control system 52 is arranged to adjust the range control collar 160 downwardly (i.e. in the distal direction) when signals are produced in the control system indicating, e.g. descent of stairs. Further adjustments of the range of flexion are preferably performed in response to other indications of changing terrain.

The provision of a variable end-stop may be achieved in other ways. For instance, the dynamic piston control valve 136 can be completely closed during locomotion under control of the microprocessor in the control system 52 at different angles and times in the gait cycle. This may be required on every step, depending on selected heel height and the walking requirements.

As a further alternative, a double piston arrangement as described above with reference to FIG. 1 may be used to provide range control independently from damping resistance control, the inner piston being used to alter the piston-stroke range (flexion end-stops). This may be accomplished by moving the inner piston 26 (see FIG. 1) incrementally and precisely by means of an electrically actuated hydraulic pump (not shown), the sensor system being used to monitor the position of the piston 26 by way of a feedback loop. In this instance, the locking control valve 40 (FIG. 1) is replaced by a pump arrangement, thereby providing the means to displace hydraulic fluid between the chambers 30A, 30B so as actively to move the reference piston 26. Alternatively, the reference piston 26 may be moved in known increments from a predetermined datum position.

In yet a further embodiment, using the arrangement shown in FIG. 1, the locking valve 40 for locking the reference piston 26 may be used to facilitate incremental movement of the reference piston 26 during plantar-flexion and dorsi-flexion phases of locomotion. The forces produced during locomotion are used, in this case, physically to move the reference piston 26, valve 36 (FIG. 1) being closed at appropriate times. The control system 52 coordinates valve actuation and monitors the reference piston position.

Figure 7:
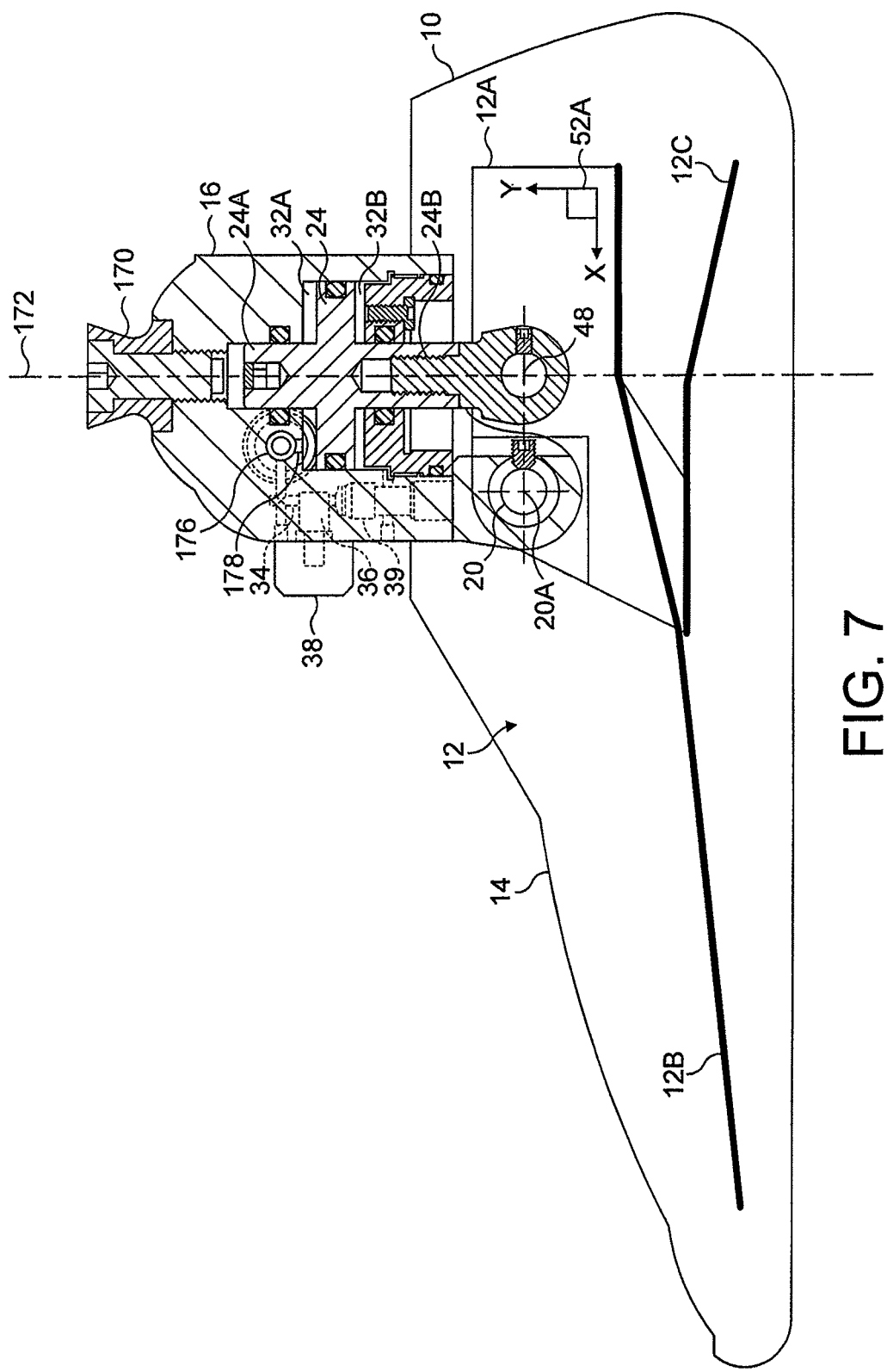
FIG. 7 is a sectional view of a fourth ankle and foot combination in accordance with the invention.

Referring to FIG. 7, another single piston embodiment of the invention has a shin component in the form of a pyramid-shaped shin connection interface 170 which defines a shin connection axis 172. As in the embodiment described above with reference to FIG. 1, an ankle joint mechanism 18 connects the shin component to the foot keel 12A of the foot 10, the mounting to the foot keel 12A being by way of an ankle flexion pivot 20 defining a flexion axis 20A.

The body of the joint mechanism 16 forms the cylinder of a piston and cylinder assembly having a piston 24 with upper and lower piston rods 24A, 24B, the lower piston rod being pivotally connected to the foot keel 12A at a second pivotal connection 48, this second pivotal connection defining a second medial-lateral axis which is spaced, in this case, posteriorly from the flexion axis 20A. It will be seen that, as the body of the mechanism 16 pivots about the flexion axis 20A, the piston 24 moves substantially linearly in the cylinder formed by the mechanism body.

The cylinder is divided into upper and lower chambers 32A, 32B. These chambers are linked by two bypass passages in the ankle mechanism body 16, one of which is visible in FIG. 7, where it is shown by dotted lines since it is behind the sectioning plane of the drawing. The other passage does not appear in FIG. 7 since it is located in front of the sectional plane. However, its configuration is almost identical, as will be described below. These two bypass passages communicate with the upper chamber 32A of the cylinder via a locking valve 176, described in more detail below, as a common linking passage 178 which opens into the upper chamber 32A.

The two bypass passages, one of which 34 is shown in FIG. 7, each contain a damping resistance control valve 36 which has an associated actuator in the form of a servo motor 38. Operation of the servo motor 38 rotates a valve member of the valve 36 to progressively increase or decrease the orifice area of the valve 36. The bypass passage 34 also contains a non-return valve 39. This adjustable-area orifice valve 36 and the non-return valve 39 are arranged in series in the bypass passage 34, between the locking valve 176 and the lower chamber 32B.

The bypass passage 34 appearing in FIG. 7 has its non-return valve 39 oriented to allow the flow of hydraulic fluid from the lower chamber 32B to the upper chamber 32A. The other bypass passage (not shown) has its non-return valve oriented in the opposite direction. Accordingly, one of the passages 34 is operative during dorsi-flexion and the other during plantar-flexion. When the locking valve 32 is open, continuous yielding movement of the foot component 10 relative to the ankle joint mechanism 16 about the flexion axis 20A is possible between dorsi-flexion and plantar-flexion limits defined by the abutment of the piston with, respectively, the lower wall and the upper wall of the cylinder containing the piston. The level of damping for dorsi-flexion and plantar-flexion is independently and automatically presettable by the respective adjustable-area orifices by means of a control system (not shown in FIG. 7) like that described above. The control system, as in the embodiments described above with reference to FIGS. 1 and 5, has a sensor 52A in the form of an accelerometer mounted on the foot keel 12A.

The shin connection interface 170 is conventional, being of pyramid construction. Typically, a shin tube is mounted to the shin connection interface 170, the shin component having, at its distal end, an annular female pyramid receptacle having alignment screws, as well known to those skilled in the art, for adjusting the orientation of the shin tube relative to the ankle joint mechanism 16. At a neutral alignment position, the axis of the shin tube (the shin axis) is coincident with the shin connection axis 172 (shown in FIG. 7). When the shin tube is affixed to the ankle unit 16 in this neutral position, the limit of dorsi-flexion of the ankle-foot prosthesis, defined by the abutment of the piston 24 with the lower wall of the lower cylinder chamber 32B, corresponds to an anterior tilt of the shin axis relative to the vertical when the user stands on a horizontal surface. The plantar flexion limit, defined by abutment of the piston 24 with the upper wall of the upper cylinder chamber 32A corresponds to a posterior tilt of the shin axis.

In this embodiment, the anterior and posterior tilt angles of the shin connection axis 22 at the dorsi-flexion and plantar-flexion limits are 4 degrees (anterior) and 8 degrees (posterior) respectively with respect to the vertical.

In this embodiment, the mechanical end-stops represented by the abutment of the piston with the lower and upper cylinder walls define a yield range over which the ankle-foot prosthesis is free to flex during locomotion and during standing, providing the locking valve 176 is open. In this respect, the lower and upper cylinder walls define a yield range in the same way as the collar 160 of the mechanism described above with reference to FIG. 6. Heel-height adjustment may be performed by altering the shin tube alignment. Alteration of the shin component alignment at the shin connection interface 170 does not alter the angular magnitude of the yielding range because it is governed by the piston stroke, but it does alter the position of the flexion range limits with respect to the vertical.

It will be understood, therefore, that the angular range magnitude is fixed by the construction and geometry of the ankle-foot prosthesis and its hydraulic joint mechanism. The degrees of dorsi-flexion and plantar-flexion respectively are altered by the alignment of the shin component connection, as described above. It will be understood that alternative alignment interfaces can be used to adjust the positions of the dorsi-flexion and plantar-flexion limits. For instance, an anterior-posterior tilt alignment interface may be provided between the ankle unit 16 and the foot keel 12. Such an interface is provided by a further embodiment of the invention, as will now be described with reference to FIGS. 8 and 9.

Figure 8:
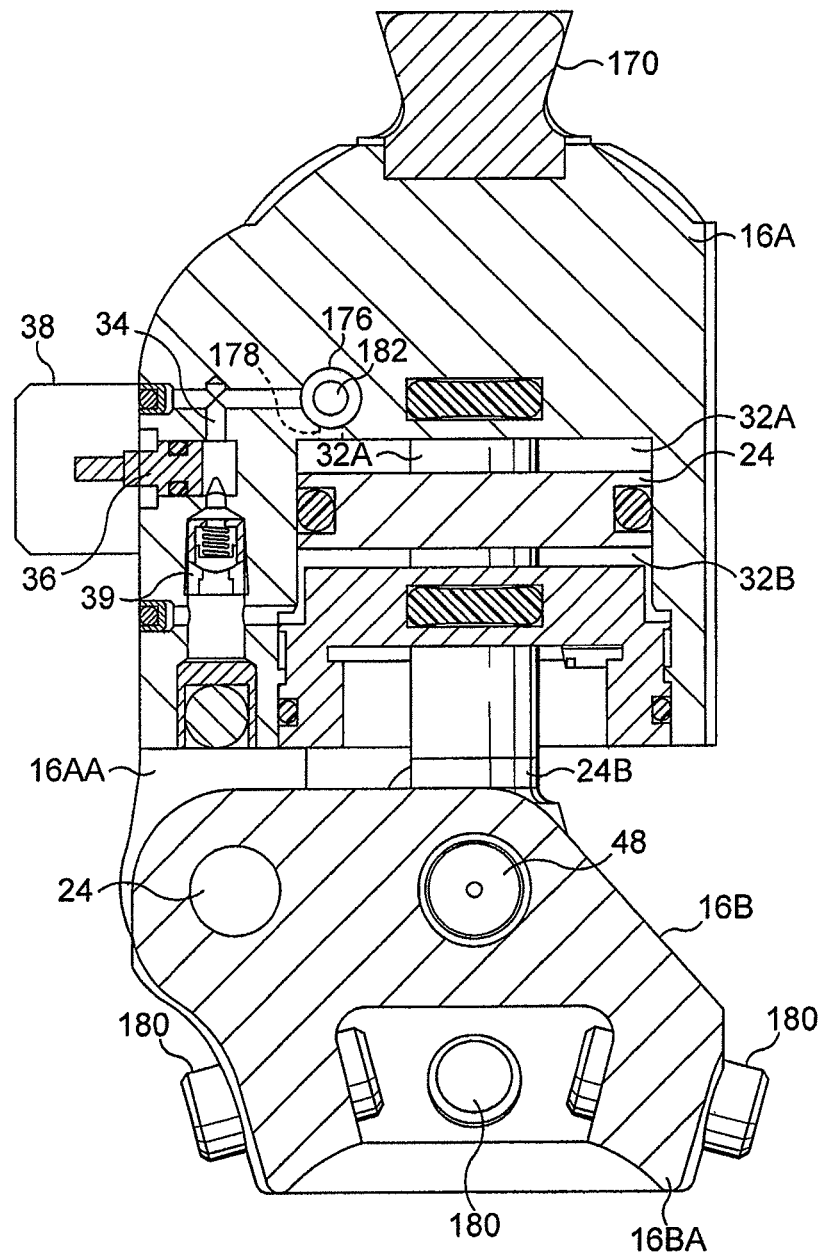
FIG. 8 is a cross-section of an ankle joint mechanism similar to that shown in FIG. 7, sectioned on an AP plane.

Referring to FIG. 8, this further embodiment of the invention takes the form of a two-part ankle joint-mechanism having an ankle unit body 16A which, as before, mounts a shin connection interface 170 for adjustable connection to a shin tube (not shown), and a foot mounting component 16B which incorporates a foot connection interface for receiving a pyramid connector of the known kind on a foot keel (not shown in FIG. 8). The joint mechanism is identical to that described above with reference to FIG. 7 with the exception that the flexion and piston rod connection pivots 20, 48 are housed in the foot mounting component 16B rather than directly in the keel of a prosthetic foot. In the case of FIG. 8, the drawing is a cross-section on a vertical anterior-posterior plane parallel to but spaced from the axis of the shin connection interface 170 and the cylinder housing the piston 24. Consequently, the bypass passage permitting hydraulic fluid flow from the lower chamber 32B to the upper chamber 32A of the cylinder (corresponding to dorsi-flexion, i.e. clockwise rotation of the foot mounting component 16B relative to the ankle unit body 16A about the pivot 20) appears in full lines, whereas the common linking passage 178 between the control valve 176 and the upper chamber 32A is shown with dotted lines.

It will be understood that the non-return valve 39 has a counterpart non-return valve in the bypass passage (not shown) allowing for plantar flexion, but that the orientation of that counterpart valve is reversed from that shown in FIG. 8, as described above with reference to FIG. 7.

For the avoidance of doubt, it should be pointed out that the bores in the ankle unit body 16A which house the upper and lower piston rods 24A, 24B provide sufficient clearance around the piston rods to allow a limited degree of rocking of the piston 24 and piston rods 24A, 24B relative to the cylinder as the foot mounting component 16B rotates with respect to the ankle unit body 16A. The periphery of the piston 24 is shaped so as to have an arcuate cross-section, also for this reason. The same features are present in the ankle unit of FIG. 7.

The distal part of the ankle unit body 16A is in the form of a trunnion 16AA housing pivot axles of the flexion pivot 20 and the piston rod connection pivot 48. The foot mounting component 16B has an integral annular female pyramid alignment coupling 16BA. This annular pyramid connector includes four screws 180, three of which are shown in FIG. 8.

Figure 9:
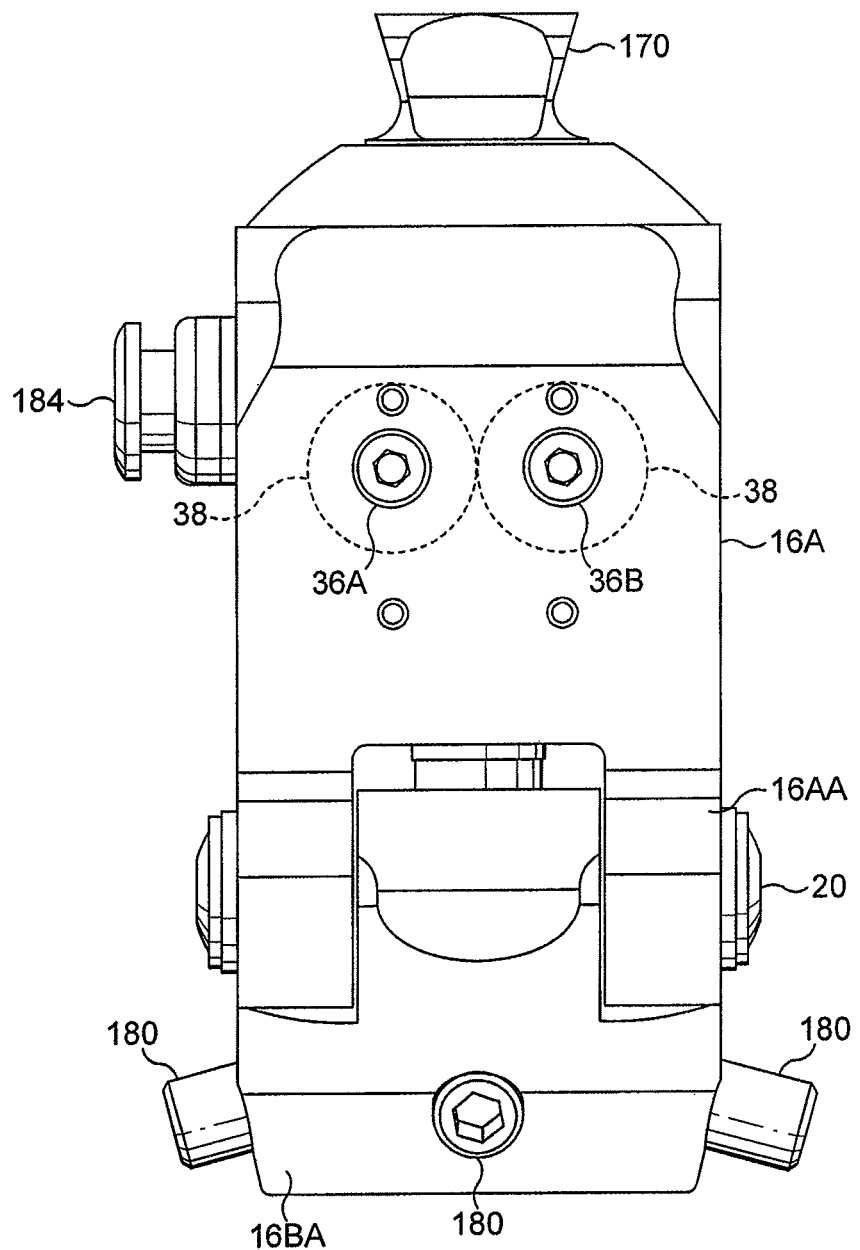
FIG. 9 is an anterior elevation of the ankle joint mechanism of FIG. 8.

The ankle unit trunnion 16AA is shown more clearly in FIG. 9. Also visible in FIG. 9 are two valve adjustment spindles 36A, 36B which are accessible on the anterior face of the ankle unit body 16A. These form part of the dynamic damping control valves 36 (or flow resistance adjusters), one of which appears as valve 36 in FIG. 8, and permit continuous electronic adjustment of damping resistance to ankle flexion in the dorsi- and plantar-flexion directions respectively. The servo motors 38 are shown by dotted lines in FIG. 9 in order that the positions of the valve spindles 36A, 36B can be more clearly seen.

Referring again to FIG. 8, the locking valve 176 is a spool valve having a spool member 182 which is slidable in a spool valve bore. The bore has three ports (not shown). A first port is that of the common linking passage 178 communicating with the upper chamber 32A of the cylinder. Second and third ports, offset medially and laterally with respect to the common passage 178, provide for communication with the bypass passages 34.

At one end of the spool member 182, there is a manually operable pushbutton 184 (see FIG. 9), which, when pushed against the outward biasing force of a stack of spring washers encircling the spool member, moves the spool member 182 to an open position, as shown in FIG. 4.

When the spool member 182 is in its open position, it allows fluid flow between the bypass passages 34 and the common passage 178 communicating with the upper chamber 32A of the cylinder. Conversely, when the push button 184 is released, the spool member 182 moves to prevent fluid flow between the upper cylinder chamber 32A and the bypass passages 36. It follows that when the pushbutton 184 is released, the ankle unit is hydraulically locked at whichever flexion angle existed at the moment of release. The pushbutton 184 has a detent that allows it to be maintained in its depressed position. This is the normal position of the locking valve 176, in which flow of hydraulic fluid through the bypass passages 36 (FIG. 8) is allowed, with the result that the ankle unit allows yielding dorsi- and plantar-flexion.

The same locking valve arrangement is present in the ankle joint mechanism of the foot-ankle prosthesis described above with reference to FIG. 7.

Figure 10:
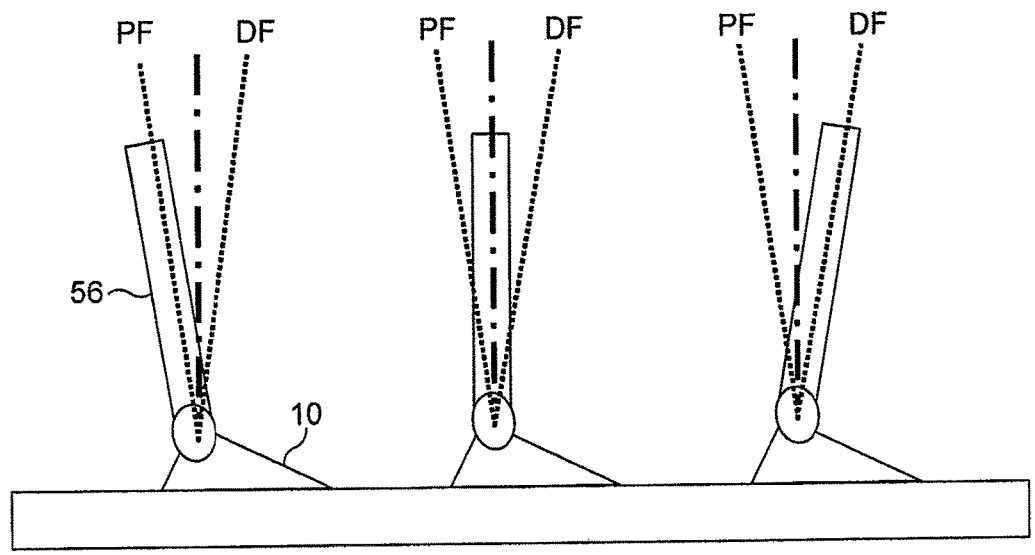
FIG. 10 is a diagram illustrating the ankle yielding range afforded by a prosthesis in accordance with the invention.

Whether the ankle unit is in the form of a two-part assembly for detachable mounting to a foot component, as described above with reference to FIGS. 8 and 9, or in the form of an ankle joint mechanism directly pivotally mounted to a prosthetic foot, as described above with reference to FIG. 7, the joint mechanism allows yielding ankle flexion as shown diagrammatically in FIG. 10. The dotted lines denote plantar-flexion (PF) and dorsi-flexion (DF) limits of a mechanical hydraulic yielding range of flexion of a shin component 56 with respect to a foot component 10. The magnitude of the angular range is fixed by the geometry of the joint mechanism and its damping piston and cylinder assembly. Although in these preferred embodiments, the range magnitude is fixed, the position of the limits with respect to a neutral position indicated by the chain lines in FIG. 10 can be altered by adjusting the alignment of the shin component relative to the foot component using one of the alignable connection interfaces described above. In this way, the flexion range may be biased anteriorly or posteriorly from the position shown in FIG. 10 to create a larger range of motion in either the PF or DF direction. Typical alignment settings result in a dorsi-flexion limit at 2 degrees to 6 degrees tilt anteriorly with respect to the neutral axis, dependent on the foot toe spring stiffness in particular, and the plantar flexion limit at 4 degrees to 10 degrees tilt posteriorly with respect to the neutral axis (shown by the chain lines in FIG. 10).

Providing the manual hydraulic lock is not activated, the unit continuously allows yield in the dorsi-flexion direction (and plantar-flexion direction) up to the dorsi-flexion limit during walking and standing.

The applicants have found that providing a yielding ankle with minimal, preferably zero elastic biasing in the dorsi- or plantar directions, and with flexion limits set within the above ranges, provides advantages during stair walking and ramp walking activities, and during standing. In the normal body, the biomechanics of standing balance control are characterised by the natural balancing of external moments between joint centres of rotation. The geometrical position of the joint centres of rotations and the relative position of the body centre of gravity and the reaction vector are important for stabilising action. Limb stability with a prosthetic limb is primarily dependent on geometry, not muscle-induced internal moments. Consequently, standing can be achieved for long periods with minimal muscular effort. A small amount of cyclical postural sway of the upper body also helps to create stability. It follows that natural standing posture and balance control can be achieved with joints exhibiting low levels of internal resistive torque, the position of the ground reaction vector relative to the hip, knee and ankle joints being the main source of limb stability. Allowing yield in a prosthetic ankle in the manner provided by the ankle-foot combination described above aids this function for a lower limb amputee.

Figure 11:
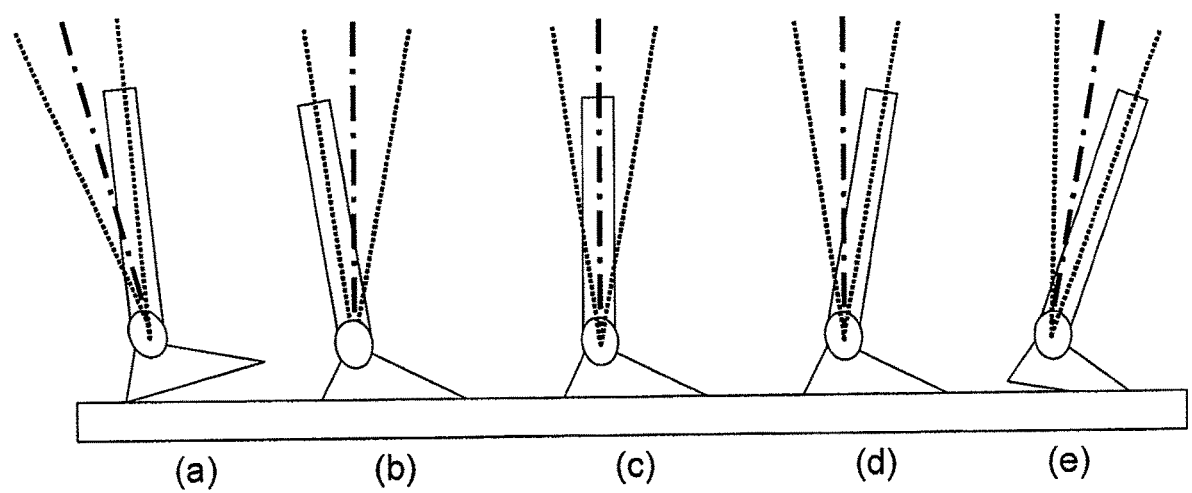
FIG. 11 is a diagram illustrating operation of a prosthesis in accordance with the invention during walking.

The dynamic action of a lower limb prosthesis having the features described above during the stance phase of walking is now described with reference to FIG. 11. At heel strike (a), the ankle is in a dorsi-flexed state from the roll-over actions of the previous step. As the foot moves towards the flat-foot state (b), the ankle plantar-flexes under the action of the foot heel spring and hydraulic yield at the ankle. In general, plantar-flexion at the ankle does not reach the plantar-flexion limit imposed by the joint mechanism of the prosthesis at this stage. During roll-over (c), the ankle begins to dorsi-flex by way of the hydraulic yield afforded by the prosthesis, providing a smooth roll-over action, preserving body momentum, and improving knee function. Towards the end of the roll-over phase (d), the dorsi-flexion limit imposed by the joint mechanism is reached. Once this happens, mechanical energy is directed into the keel of the foot (e) to provide energy return for push-off. The swing phase is initiated with the foot oriented at the dorsi-flexion end-stop to provide toe clearance during the swing phase.

The combination described with reference to the FIGS. 7 to 11 is an foot-ankle system that is continuously allowed to yield over a limited range in plantar-flexion and dorsi-flexion. The yielding action is provided by a hydraulic damper coupled to conventional foot elements (i.e. keel, carrier and independent carbon fibre composite heel-toe springs). The ankle is, therefore, free to flex continuously over a limited plantar- and dorsi-flexion range via the hydraulic damper with minimal interference from elastic elements during walking and standing. During standing, the relative positions of the hip, knee and ankle joint centres are such that substantially normal standing postures can be maintained, the moments about each joint being automatically balanced thereby creating limb stability. Moreover, the self-aligning action of the foot-ankle system facilitates improved control of energy transfer between limb segments during locomotion, the user's hip joint being the main driver and the knee joint being the main facilitator of mechanical energy transfer. This biomimetic method of stabilisation of standing stability and balance control has a further advantage in that, while standing on ramps, owing to the yielding action of the hydraulic components, there are no significant reaction moments generated around the ankle which may cause imbalance between joints and discomfort. Since, owing to the limited range of hydraulic yielding, the ankle is free to move, adaptation for walking and standing on inclined surfaces and changes to footwear with various heel heights is achieved automatically. A further advantage of the system is a smoother more progressive transition during roll-over a variety of terrains.

In all the control embodiments described above, it is preferable that functional parameters such as plantar-flexion and dorsi-flexion resistance levels, profiles (i.e. resistance alteration gradients with respect to time) and timing, as well as dorsi-flexion range of motion are programmably adjustable. Each of the embodiments may include within the control system 52 a receiver for communication with a wireless programming device (not shown). Wireless programming may be performed by a prosthetist during an amputee walking test and tests over different terrains (e.g. stairs and inclined surfaces) to adjust control parameters which may or may not be pre-selected by means such as a look-up table to suit the particular amputee's specific locomotion style and the mechanical properties of attached foot and knee components. Similarly, adaptive control parameters which determine how the above functional parameters are continuously adapted during locomotion and use, such as walking speed, walking surface gradient, and activities such as stair climbing and descent, are also adjustable under prosthetist control, using control software. Specified and/or measured adaptive control parameter values may be entered. This may be achieved using a teaching/playback system. It is also possible to incorporate a self-tuning system whereby control parameters are automatically adjusted towards specific values under known walking conditions. The changes in damping response may be predefined and contained in a database stored in a storage device forming part of the control system 52, the database being drawn from clinical experience and tests with a plurality of amputees. Teaching/playback, database, and self-tuning look-up methods may be used in combination.

The timing of control of valve function and/or other associated dorsi-flexion limiting means are preferably coordinated during locomotion to occur at specific phases of the gait cycle determined from system sensors and using finite state control principles. In this way the control system can be readily adapted to optimize the mechanical characteristics of the prosthesis, thereby to optimize the biomechanics of locomotion.

Figure 12A:
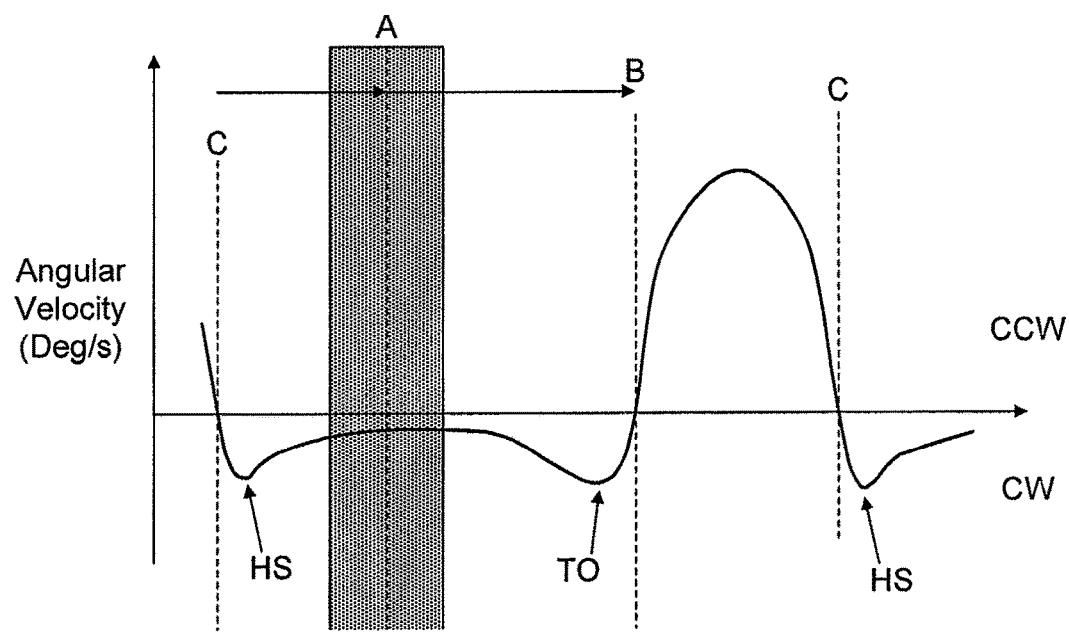
FIGS. 12A and 12B are graphs illustrating the dynamic control of damping resistance during an individual gait cycle.
Figure 12B:
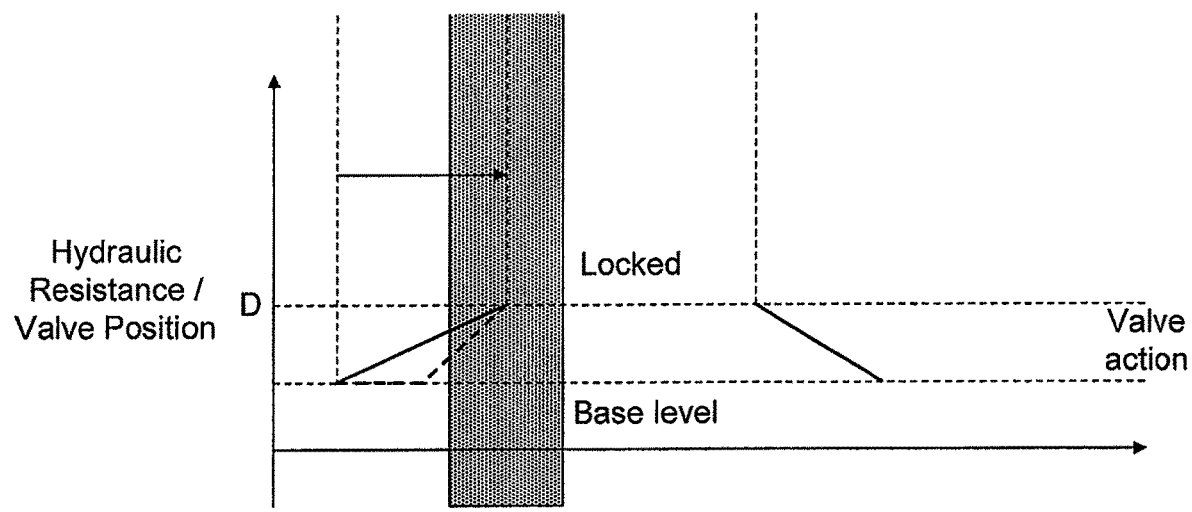

Referring now to FIGS. 12A and 12B, hydraulic flexion damping resistance and end-stop control may be achieved using a single electrically controlled valve. FIG. 12A is a graph plotting the angular velocity of the shin component in the sagittal plane during locomotion, obtained from a gyroscope sensor. Control valve and actuator adjustments are coordinated with respect to detection of gait events such as heel strike (HS) and toe-off (TO), as shown in FIG. 12A using, for instance, zero-crossing trigger points B, C representing the transition between counter-clockwise (CCW) and clockwise (CW) angular movement of the shin component. In FIG. 12A, the vertical axis represents shin angular velocity and the horizontal axis represents time, the graph showing a complete gait cycle. Thus, control valve and actuator adjustments can be coordinated with respect to detected gait events, such as signal zero-crossing events or local signal maxima and minima.

FIG. 12B illustrates damping control valve actuation from a base resistance level B, a fully closed position D in which the associated piston is locked. The shaded region A illustrates an adjustment range for commencement of the locked state during the stance phase, resistance to flexion in the dorsi-flexion direction increasing following heel strike to a time A which is at a predetermined time interval after a trigger point C represented by the zero-crossing of the shin angular velocity characteristic prior to heel strike HS. Lock commencement at time A is delayed when the control system 52 detects walking on an incline or stairs (compared to level walking). Thus, flexion is restricted and/or limited angularly with respect to heel strike. In effect, gait-cycle by gait-cycle actuation of the valve as shown in FIG. 12B provides variable dorsi-flexion angular limitation. The dotted line in FIG. 12B indicates alteration of the resistance gradient in response to sensed locomotion characteristics.

The range of motion limit may be specified to occur in response to measured characteristics of locomotion such as shin component tilt angle, velocity, or acceleration. Other kinematic or kinetic measurements made during locomotion may be used.

Over at least the major part of the range of ankle movement, the damping resistance in the direction of dorsi-flexion remains substantially constant during each step of the locomotion cycle. However, the level of damping resistance is allowed to change from step to step according to signals generated in the control system in response to sensor outputs. The same applies to the damping resistance in the direction of plantar-flexion. In general, at any point within the range of ankle movement, the damping resistance can be set to any of several different values in response to such control system signals. Indeed, the level of damping resistance in both dorsi-flexion and plantar-flexion directions is continuously variable over a range of resistance level values, the limits of the resistance level range being determined by the maximum and minimum orifice areas of the dynamic damping control valves.

The control system may be programmed to alter damping resistance from step to step in a number of different ways. In one configuration the change in damping resistance in the directions of both dorsi-flexion and plantar-flexion are linearly related to a sensed parameter. For instance, as shown in FIG. 13A, the damping control valves can be adjusted linearly between their open and closed positions according to surface inclination. The damping levels and the valve settings indicated in FIG. 11A at A represent the dynamic plantar-flexion/dorsi-flexion balance set for level walking.

Referring to FIG. 13B, the control system may be programmed such that the optimum dorsi-flexion and plantar flexion damping levels are unequal for level walking. Such levels are determined by programming the control system to suit an individual amputee's preferred walking characteristics. As shown in the example of FIG. 13B, the optimum level of resistance to rotation in the direction of dorsi-flexion is less than that in the direction of plantar-flexion. However, according to the requirements of the amputee, the opposite may also be true.

Either or both the resistance in the direction of dorsi-flexion and the resistance in the direction of plantar-flexion may be non-linearly related to the sensed surface inclination. In the example shown in FIG. 13C, the response in the direction of plantar-flexion is non-linearly related to surface inclination, while the response in the direction of dorsi-flexion is linear. Either one or both of plantar-flexion and dorsi-flexion responses may be non-linear or linear according to the value of the sensed parameter.

It will be noted that in each of the above examples, the resistance in the direction of plantar-flexion increases with increasing upward surface inclination and decreased with increasing downward surface inclination, whereas the resistance in the direction of dorsi-flexion varies in the opposite sense.

Typical responses in damping resistance to changes in walking speed are shown in FIG. 13D. As will be seen, at a normal walking speed or cadence, the resistance in the direction of dorsi-flexion in this example is higher than the resistance to plantar-flexion. As walking speed or cadence increases, the resistance in the direction of plantar-flexion increases whilst that in the direction of dorsi-flexion decreases. The converse changes apply at slower walking speeds or cadences. In this case, the variation in damping resistances is linear. Non-linear functions may also be programmed in the control system.

In the preferred system, the settings of damping resistance remain constant over at least the major part of the range of ankle movement, and change from step-to-step according to changes in the sensed parameter using the functions described above with reference to FIGS. 13A to 13D. For a given heel-height setting, the range of ankle joint motion may be fixed, or it may be varied using variable hydraulic of mechanical end stops, as described above.

The changes in walking requirements may be determined on an individual step-by-step basis or they may be determined based upon a measured average of a previous number of steps of a specific variable such as walking speed, cadence, surface inclination or other measured gait variable.

The control system may be programmed to divide the range of sensed or computed parameter values into bands or sub-ranges, so that changes in damping resistance are triggered only when the relevant parameter value changes to the extent that it falls within a different range from previously. The overall range of values of the sensed or computed parameter may be divided linearly as shown by the uniform spacing of surface inclination or walking speed values in the graphs of FIGS. 13A to 13D, or non-linearly, for instance according to a square law or a logarithmic function. In other words, the boundaries between bands may be uniformly or non-uniform. They may also be preset or continuously adaptive according to stored gait characteristic histories. Non-linear relationships between damping resistance and the sensed or computed parameter typically result in increasingly large changes in resistance level as the value of the controlled parameter deviates further from a central value (i.e. from level surface inclination or normal walking speed, for instance).

Figure 14A:
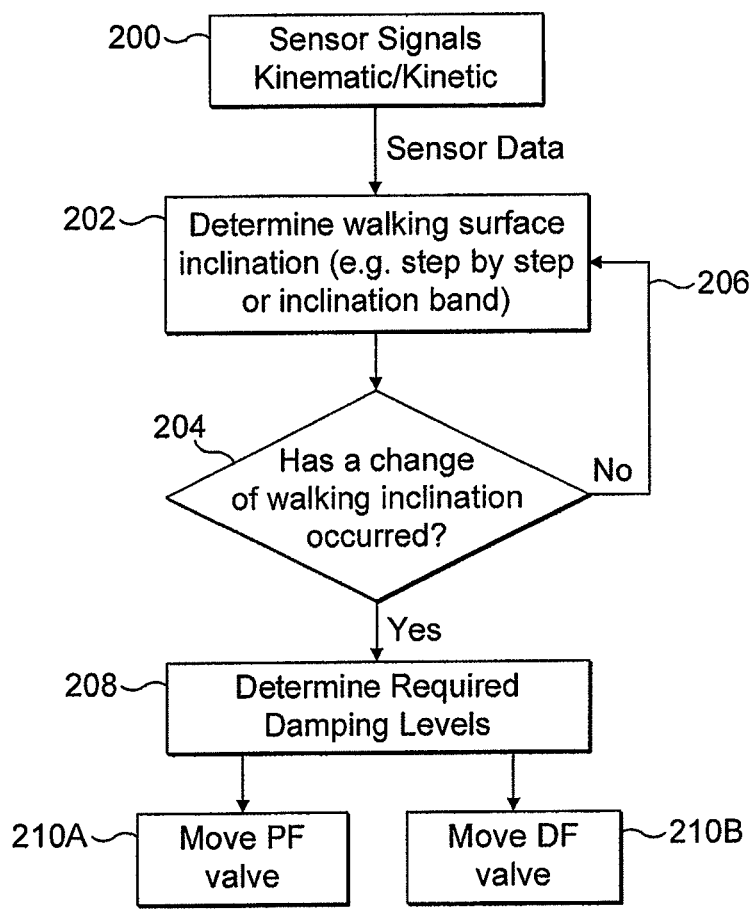
FIGS. 14A and 14B are flow diagrams for dynamic damping control in response to walking surface inclination and a combination of walking requirements respectively.

The control system may be programmed to follow different sequences for the purpose of adjusting valve openings in response to changes in sensed or computed parameters. Referring to FIG. 14A, a first typical sequence for adapting valve openings to sensed walking surface inclination involves the steps of reading sensor signals indicative of kinetic or kinematic parameter values (step 200), computing the walking surface inclination, preferably on a step-by-step basis, the inclination being compared to preset inclination bands (step 202), whereupon the system then determines whether a change in inclination has occurred (step 204). If no change has occurred, the sequence loops back (loop 206) to repeat the determination of surface inclination and comparison steps 202, 204, this process continuing until a change is detected. When a change is detected, required damping resistance levels are computed, e.g. by reference to a look-up table mapping resistance levels to parameter bands (step 208), whereupon actuating signals are fed to the servo motors (or stepper motors) connected to the valves which control damping resistance to ankle rotation in the direction of plantar-flexion and dorsi-flexion respectively (steps 210A, 210B).

Figure 14B:
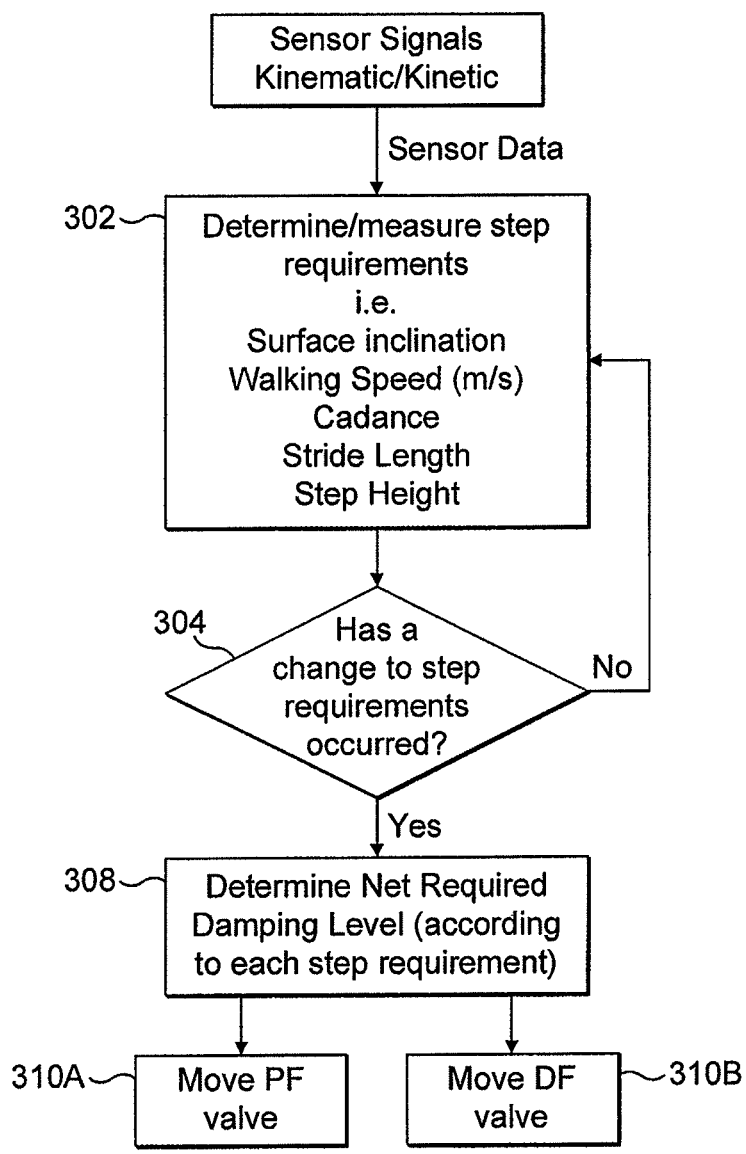

In a more sophisticated control sequence, shown in the flow diagram of FIG. 14B, similar steps are performed. In this case, the initial determination step 302 involves the computation of any of a number of parameters, including surface inclination, walking speed, cadence, stride length and step height (for climbing or descending stairs). Each derived parameter is then compared with previously stored values (step 304) and, if a change has occurred, net required damping levels are computed according to pre-programmed rules in order to move the damping control valves (steps 310A, 310B).

The prostheses described above incorporate one or both of an accelerometer mounted on the keel of the foot component and a magnetic positional sensor for piston position sensing. Accelerometers may be mounted in other locations, for instance on a shin tube. Rotary or linear position sensors may be used. Strain gauge sensors may be used to measure ankle forces and moments. Piezoelectric bending sensors may be incorporated for measuring energy storage within foot springs (e.g. toe spring 12B (FIG. 1)). Such piezoelectric devices may be used for generating electrical energy (e.g. for charging batteries supplying power to the control system 52 (FIG. 1)). In this way, electrical energy may be generated on every step.

In the preferred embodiments of the invention, optimum levels of damping resistance in the directions of plantar-flexion and dorsi-flexion are obtained to provide an adaptive dynamic balance which suits an individual amputee's gait in different situations and for different walking requirements. The nature of the adaptive dynamic balance is that it has the effect of acting like a brake and an accelerator on the motion of the shin. Optimising these effects for different walking situations produces a more stable gait, placing less physiological demand on the amputee to control proximal joints, i.e. the knee and/or the hip through muscular control, and also with reduced stress at the stump interface.

What is claimed is:

1. A prosthetic ankle and foot combination comprising a foot component and an ankle joint mechanism, the ankle joint mechanism including a shin component and being constructed to allow damped rotational movement of the foot component relative to the shin component about a medial-lateral joint flexion axis, wherein:

the ankle joint mechanism is arranged to provide a continuous hydraulically damped range of ankle motion during walking with dynamically variable damping resistances associated with ankle motion in plantarflexion and dorsiflexion directions respectively;

the combination further comprises a control system coupled to the ankle joint mechanism having a plurality of sensors for generating signals indicative of a kinematic parameter of locomotion and walking environment; and the ankle joint mechanism and the control system are arranged such that the damping resistances effective over the said range of motion and associated with motion in the plantarflexion and dorsiflexion directions are adapted automatically in response to the said signals, wherein the control system is arranged to generate signals indicative of ground inclination and to cause the damping resistance in the direction of dorsiflexion to be increased to a maximum value, to limit dorsiflexion in stance phase phases of first and second gait cycles, wherein the signals are indicative of walking on level ground during the first gait cycle, wherein the signals are indicative of walking down stairs or up an incline during the second gait cycle, and wherein the damping resistance in the direction of dorsiflexion is programmably adjustable and is increased to the maximum value later in the stance phase of the second gait cycle than in the stance phase of the first gait cycle.

2. A prosthetic ankle and foot combination as claimed in claim 1, wherein the control system is further arranged to generate signals indicative of speed of locomotion; wherein the control system is arranged to generate the signals indicative of ground inclination and to cause the damping resistance in the direction of dorsiflexion to be increased to a maximum value, to limit dorsiflexion in a stance phase of a third gait cycle; wherein the signals indicative of ground inclination are indicative of walking on level ground during the third gait cycle; wherein the signals indicative of speed of locomotion are indicative of a first speed of locomotion during the first gait cycle and a third speed of locomotion during the third gait cycle, wherein the third speed of locomotion is greater than the first speed of locomotion.

3. A prosthetic ankle and foot combination as claimed in claim 1, wherein the ankle joint mechanism is locked when the damping resistance in the direction of dorsiflexion is increased to the maximum value.

4. A prosthetic ankle and foot combination as claimed in claim 1, arranged such that damping resistance is the predominant resistance to ankle joint flexion over at least part of the said range of ankle motion.

5. A prosthetic ankle and foot combination as claimed in claim 1, wherein the ankle joint mechanism comprises a hydraulic piston and cylinder assembly and an associated linkage arranged to convert between translational piston movement and rotational relative movement of the foot component and the shin component, the piston and cylinder assembly including at least one adjustable damping control valve arranged to vary a degree of hydraulic damping resistance to the said translational piston movement, and wherein the ankle joint mechanism further comprises an actuator coupled to the at least one valve for adjusting the valve during locomotion.

6. A prosthetic ankle joint assembly comprising a proximal mounting interface, a distal mounting interface, and a joint mechanism interconnecting the proximal and distal mounting interfaces and constructed to allow damped rotational movement of the distal mounting interface relative to the proximal mounting interface about a medial-lateral joint flexion axis, wherein:

the joint mechanism is arranged to provide a continuous hydraulically damped range of ankle motion during walking with dynamically variable damping resistances associated with ankle motion in plantarflexion and dorsiflexion directions respectively;

the ankle joint assembly further comprises a control system coupled to the joint mechanism having a plurality of sensors for generating signals indicative of a kinematic parameter of locomotion and walking environment; and the joint mechanism and the control system are arranged such that the damping resistances effective over the said range of motion and associated with motion in the plantarflexion and dorsiflexion directions are adapted automatically in response to the said signals, wherein the control system is arranged to generate signals indicative of ground inclination and to cause the damping resistance in the direction of dorsiflexion to be increased to a maximum value to limit dorsiflexion in stance phases of first and second gait cycles wherein the signals are indicative of walking on level ground during the first gait cycle, wherein the signals are indicative of walking down stairs or up an incline during the second gait cycle, and wherein the damping resistance in the direction of dorsiflexion is programmably adjustable and is increased to the maximum value later in the stance phase of the second gait cycle than in the stance phase of the first gait cycle.

7. A prosthetic ankle joint assembly as claimed in claim 6, wherein the control system is further arranged to generate signals indicative of speed of locomotion; wherein the control system is arranged to generate the signals indicative of ground inclination and to cause the damping resistance in the direction of dorsiflexion to be increased to a maximum value to limit dorsiflexion in a stance phase of a third gait cycle; wherein the signals indicative of ground inclination are indicative of walking on level ground during the third gait cycle; wherein the signals indicative of speed of locomotion are indicative of a first speed of locomotion during the first gait cycle and a third speed of locomotion during the third gait cycle, wherein the third speed of locomotion is greater than the first speed of locomotion.

8. A prosthetic ankle joint assembly as claimed in claim 6, wherein the joint mechanism is locked when the damping resistance in the direction of dorsiflexion is increased to the maximum value.

9. A prosthetic ankle joint assembly as claimed in claim 6, arranged such that damping resistance is the predominant resistance to ankle joint flexion over at least part of the said range of ankle motion.

10. A prosthetic ankle joint assembly as claimed in claim 6, wherein the joint mechanism comprises a hydraulic piston and cylinder assembly and an associated linkage arranged to convert between translational piston movement and rotational relative movement of the distal mounting interface and the proximal mounting interface, the piston and cylinder assembly including at least one adjustable damping control valve arranged to vary a degree of hydraulic damping resistance to the said translational piston movement, and wherein the joint mechanism further comprises an actuator coupled to the at least one valve for adjusting the valve during locomotion.

\* \* \* \* \*